United States Patent [19]

Hollis et al.

[11] Patent Number: 5,538,885
[45] Date of Patent: Jul. 23, 1996

[54] EXPRESSION SYSTEMS

[75] Inventors: Melvyn Hollis; Maurice R. C. Needham; Clare Gooding, all of Cheshire; Franklin G. Grosveld; Michael Antoniou, both of London, all of England

[73] Assignee: Imperial Chemical Industries PLC, London, United Kingdom

[21] Appl. No.: 186,895

[22] Filed: Jan. 27, 1994

Related U.S. Application Data

[63] Continuation of Ser. No. 46,383, Apr. 9, 1993, abandoned, which is a continuation of Ser. No. 810,414, Dec. 20, 1991, abandoned.

[30] Foreign Application Priority Data

Dec. 21, 1990 [GB] United Kingdom ............... 9027917

[51] Int. Cl.⁶ ..................... C12N 15/06; C12N 15/85; C12P 21/00
[52] U.S. Cl. ..................... 435/240.2; 435/69.1
[58] Field of Search ................. 435/69.1, 240.2, 435/320.1, 172.3; 536/24.1; 935/6, 34

[56] References Cited

U.S. PATENT DOCUMENTS 4,663,281  5/1987  Gillies et al. ................ 435/69.7

FOREIGN PATENT DOCUMENTS

WO89/01517  2/1989  WIPO.

OTHER PUBLICATIONS

Nevins. Ann. Rev. Biochem. 1983, (52) 441–466.

*Primary Examiner*—James Martinell
*Attorney, Agent, or Firm*—Cushman Darby & Cushman

[57] ABSTRACT

Expression systems which comprise a mammalian host, such as erythroid cells, transformed with a vector which comprises a promoter, a DNA sequence which codes for a desired polypeptide and a dominant control region. The vectors and methods for preparing polypeptides using the expression systems are also described. In a preferred embodiment, the vector contains cDNA for the desired polypeptide and a sequence which is capable of stabilising mRNA produced from the cDNA. The expression systems are particularly efficient and are capable of secreting the desired polypeptide.

6 Claims, 34 Drawing Sheets

Schematic diagrams of plasmids βH2, β-Mini and GSE 1417

Construction of plasmid pUnivec

Plasmid map of p. Univec a) Sequence of oligonucleotide used to rebuild 5' end of HGH cDNA
b) Insertion of oligo into 5' end of HGH cDNA Cloning of complete HGH cDNA/Globin cassette into GSE1417.

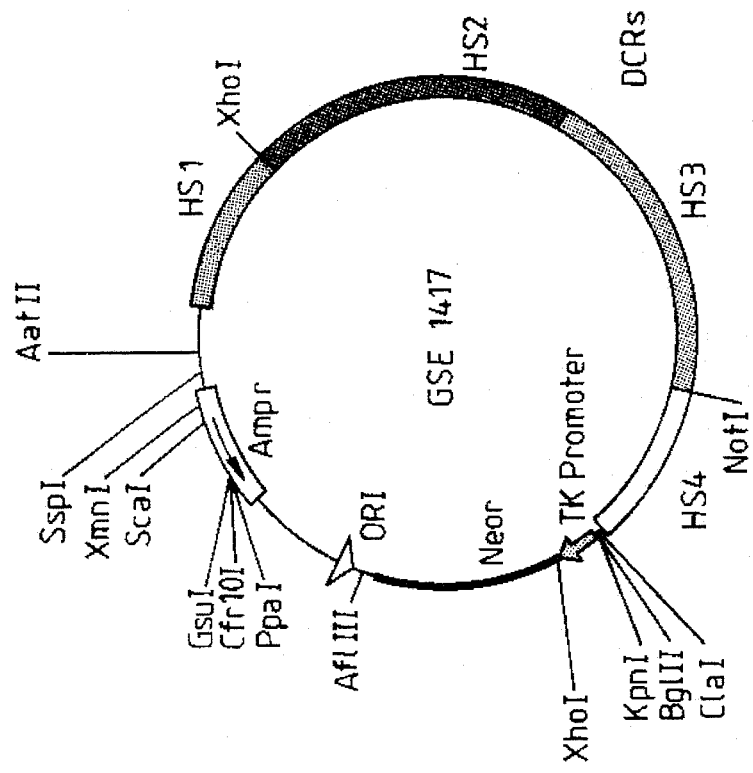
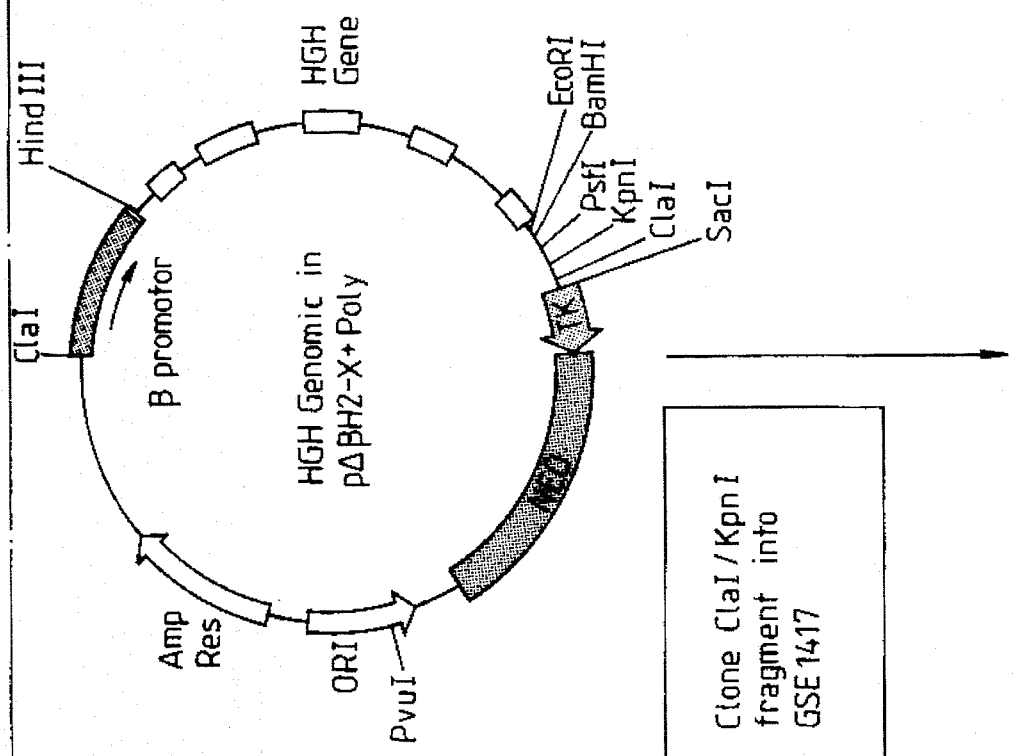
Fig. 7Cont. 1.

Construction of HGH Genomic expression construct (i)

(ii)

Replace 7kb Aat II fragment from HGH cDNA construct with 7kb Aat II fragment from HGH Genomic construct Construction of HGH cDNA/Genomic Fusion expression construct Long term expression and secretion of 2 HGH cDNA clones in MELC88 cells 6.2 kb Hind III fragment encoding entire PLA2 gene cloned into DCR expression vector 4hr exposure 4hr exposure (a)

UI Mel | 1b | 1c | 1d | 2b | 2c | 2f (b)

UI Mel | 1b | 1c | 1d | 2b | 2c | 2f

EXPRESSION SYSTEMS

This is a continuation of application Ser. No. 08/046,383, filed on Apr. 9, 1993, which was abandoned upon the filing hereof which is a continuation of application Ser. No. 07/810,414, filed Dec. 20, 1991, now abandoned.

TECHNICAL FIELD

The present invention relates to recombinant DNA technology, and in particular to methods of producing polypeptides in mammalian hosts. The present invention also relates to the vectors for use in such methods and to host cells produced from such vectors.

BACKGROUND TO INVENTION

Many biologically active proteins or polypeptides are produced in eukaryotic cells but are found in only minute quantities in their native cells or tissues. These proteins can be extremely difficult or expensive to purify in quantity, often due to the scarcity of the natural supply. Recombinant DNA methods have allowed the generation of complementary DNA (cDNA) sequences which code for the proteins of interest. These cDNAs can be inserted into cloning vectors (along with the appropriate regulatory regions necessary for expression) and introduced into suitable host cells. The introduction of such vectors into the appropriate cells allows the cells to produce the polypeptide encoded by the cDNA. Similar vectors can be made using the genomic (ie with introns and exons) sequences which make up the gene of interest. Eukaryotic cells (and in particular mammalian cells) are able to perform a number of post-translational modifications (such as amidation, glycosylation etc) which are not observed with expression in prokaryotic cells. Consequently, mammalian cells often produce proteins which resemble more closely the natural, biologically active protein molecules. The large scale culture of mammalian cells, however, is expensive and slow compared to the culture of prokaryotic cells, and methods are continually sought to increase the productivity per animal cell and to decrease the time to generate useful quantities of the protein product by the animal cell.

In general, the introduction of foreign DNA (such as the vectors described above) into animal cells leads to the random integration of one or more copies of the DNA into the genome of the cell. The level of gene expression from the foreign gene is highly dependent on the position of integration of the foreign DNA into the host genome ('position effects'). Integration into so-called 'active regions' usually produces somewhat higher levels of expression but these are often still low when compared to the levels seen with a native chromosomal (non-transfected) gene. The levels of the transfected gene do not generally correlate with the copy number in any one cell; another consequence of position effects.

A common technique used to increase the productivity of transfected host cells is the in vivo amplification of the integrated foreign DNA to produce high copy-number integrants. In these procedures, the gene of interest (along with appropriate control sequences) is co-transfected with a gene which can have a protective effect against a toxic substance. A commonly used protective gene is the dihydrofolate reductase (DHFR) gene. When increasing concentrations of methotrexate (MTX), a competitive inhibitor of the essential enzyme DHFR, is applied to the transfected cells, only cells with higher expression levels of DHFR will survive. As MTX levels are increased further, only cells which amplify the copy number of the DHFR gene (and consequently the co-transfected recombinant expression construct) will survive. In this way, the copy number and hence expression levels (ie productivity per cell) of the cDNA can be increased.

Recently, a novel enhancer-like element from the human globin locus has been described (Grosveld et al., 1987; WO 89/01517) which directs high level, position independent, copy-number dependent expression of heterologous genes in erythroid cells. This element is extremely cell-type specific and only functions in erythroid cells. This dominant control region (DCR) element has been used to overcome position effects in the expression of human β-globin in erythroid cells. This reference, WO 89/01517, describes the use of this enhancer element in the expression of β-globin from the globin promoter.

However, the use of the DCRs for expression of heterologous proteins has not become widespread because of the nature of erythroid cells and the perception that the cells are incapable of significant levels of secretion.

There is a need for a mammalian expression system which is capable of expressing heterologous polypeptides.

There is also a need for improved mammalian expression systems which are capable of expressing polypeptides at high levels.

There is also a need for a mammalian expression system which is capable of expressing a polypeptide at high levels and secreting the polypeptide expressed.

DISCLOSURE OF INVENTION

It has now been discovered that mammalian expression systems may be used to express heterologus polypeptides, and in particular that certain mammalian expression systems which include a DCR are capable of expressing polypeptides at high levels. Mammmalian expression systems have also been discovered which are capable of expressing a polypeptide at a high level, and secreting the expressed polypeptide.

Thus the present invention provides a mamalian expression system capable of expressing heterologous polypeptides.

Accordingly, the present invention provides an expression system which comprises a mammalian host transformed with a vector which comprises a promoter, a DNA sequence which codes for a desired heterologous polypeptide and a dominant control region.

The DNA sequence which codes for the desired heterologous polypeptide will, in general, comprise a gene which is a heterologous gene in the sense that it is not found in the host in nature.

The promoter may comprise any promoter which is capable of functioning in the host cell. For example, the promoter may comprise a promoter which is found in the host in nature or may comprise a heterologous promoter, that is a promoter which is not normally found in the host in nature. Examples of the former include, for example, where the host comprises erythroid cells the promoter may comprise the β-globin promoter. Examples of the latter include, for example, where the host comprises cells such as erythroid cells a promoter such as the PLA2 promoter.

Examples of preferred mammalian hosts of the present invention include, for example erythroid cells, such as mouse erythroleukaemia (MEL), rat erythreleukaemia (REL) and human erythroleukaemia cells (HEL). A particularly suitable host is MEL cells, production and characteristics of which are described by Deisseroth et al, Proceedings of the National Acadmey of Sciences, Volume 72, No. 3, p1102–1106; Deisseroth and Hendrick, Cell, 15, 55–63, 1978; and by Friend et al, Proceedings of the National Academy of Sciences, Volume 68, p378–382, 1971.

The expression system of the present invention has been found to be particularly advantageous. For example where the host comprises erythroid cells (especially MEL cells), the expression system has been found to be suprisingly advantageous. The advantages of such an expression system include, for example, that the host may be cultivated with relative ease without the need for special requirements such as high serum. Also it has unexpectedly been found that the system functions efficiently without having to select individual clones which are able to express highly. Thus the expression system of the present invention has been found to be a suprisingly efficient and flexible system.

It has further been discovered that when the host comprises erythroid cells that expression may occur with suprising efficiency. Expression may be intracellular, located within the cell wall or may be accompanied by secretion. This was unexpected. In particular it was not expected that such an expression system could be used to obtain secretion.

Expression systems have also been constructed which comprise a heterologous promoter, and such systems have found to be suprisingly efficient.

The vectors useful in providing the expression systems of the present invention provide a further feature of the present invention.

A preferred vector includes a sequence which is capable of stabilising mRNA produced from the DNA sequence which codes for the desired polypeptide. Such vectors have been found to be particularly advantageous in that they give rise to high levels of expression.

Thus according to a preferred embodiment of the present invention there is provided a vector, said vector comprising a promoter, a dominant control region, a DNA sequence which codes for a desired polypeptide, and a DNA sequence which is capable of conferring stability on mRNA produced from said DNA sequence which codes for a desired polypeptide.

It is preferred that the DNA sequence which codes for the desired polypeptide comprises cDNA.

As used herein the term "dominant control region" (or "DCR") means a sequence of DNA capable of conferring upon a linked gene expression system the property of host cell-type restricted, integration site independent, copy number dependent expression when integrated into the genome of a host compatible with the dominant control region. The dominant control region retains this property when fully reconstituted within the chromosome of the host cell; and the ability to direct efficient host cell-type restricted expression is retained even when fully reformed in a heterologous background such as a different part of the homologous chromosome or even a different chromosome.

The term "vector" as used herein is used in its broadest sense and includes within its meaning any recombinant DNA material capable of transferring DNA from one cell to another. The vector may comprise a single piece of DNA in linear or circular form.

Thus the present invention provides a vector which can be integrated into a mammalian host cell. The present invention also provides a transfer vector, such as a plasmid, which is useful, for example, in the construction of a vector for integration.

The vector may, in addition to the DNA sequences mentioned above include other DNA sequences suitable for particular applications, such as appropriate control sequences. For example the vector may include DNA sequences which allow the replication of, and selection for, the vector in a bacterial host such as E. coli. The vector may include a "selectable marker" gene which, on expression, gives a protein in an amount capable of protecting the recombinant host cell against a toxic substance. Examples of selectable markers include the neomycin and the hygromycin markers. In general the cDNA expression vector will include a polyadenylation site which is compatible with the promoter. For example, the polyadenylation site may be that of the β-globin gene, in which case it may be accompanied by sequence downstream of the β-globin polyadenylation site, for example about 2 kb of the sequence downstream from the polyadenylation site.

The promoter may comprise any promoter which is capable of functioning in the host cell. For example, the promoter may comprise the β-globin promoter or the PLA2 promoter. In one embodiment of the invention it is preferred that the promoter comprises the β-globin promoter, particularly when the host comprises ethyroid cells. In a further embodiment of the present invention it is preferred that the promoter comprises the PLA2 promoter and the host cells comprise erythroid cells.

The DNA sequence which confers stability on mRNA produced from the DNA sequence which codes for a desired polypeptide may be coupled to the DNA sequence which codes for a desired polypeptide so that hybrid mRNA is produced which is more stable than mRNA from the DNA sequence which codes for a desired polypeptide. The sequences may be coupled directly to one another or indirectly, (that is they may be contiguous or they may be separated by a further DNA sequence), provided that stability is conferred on mRNA produced from the DNA which codes for a desired polypeptide by production of a hybrid mRNA which is more stable than mRNA from the DNA which codes for the desired polypeptide.

The sequence which is capable of conferring stability on mRNA may conveniently also provide a suitable splice site which gives rise to correctly spliced RNA.

The sequence which is capable of conferring stability on mRNA may comprise an exon and an intron from a mammalian gene. Such an intron and/or exon may be present as a whole or in part.

A particular example for the sequence which is capable of conferring stability on mRNA, is a sequence which comprises the β-globin gene or a sequence derived therefrom (for example a portion of the β-globin gene), especially a sequence derived therefrom which comprises two exons and an intron, such as exon 2, intron 2 and exon 3. The or each exon and/or intron may be reduced in length, and in particular exon 2 may be reduced in length so that the sequence may comprise exon 2 or a portion of exon 2; intron 2 and exon 3.

It is generally preferred that the sequence includes the 3' end of the β-globin gene, or a portion thereof. For example the sequence may include the sequence up to the natural Xba I site at base 4845 in the β-globin gene.

The β-globin gene has been widely reported (see, for example, Lawn et al, Cell, 21, 647–651, 1980).

The cDNA sequence codes for a desired polypeptide and it may give rise, for example, to intracellular, cell surface or secreted polypeptide. Examples of cDNA sequences include human β-globin cDNA, human growth hormone cDNA, human PLA$_2$ cDNA, and human G-CSF cDNA.

It is preferred that the promoter is a heterologous promoter. When a heterologous promoter such as the PLA2 promoter is employed the level of expression obtained is suprisingly high.

The dominant control region or DCR may comprise a sequence defined in WO89/01517 (Grosveldt et al) and (referred to in that reference as a dominant activator sequence), which is incorporated herein by way of reference.

The dominant control region may be derived by recombinant DNA techniques from a naturally occurring gene system or may correspond to a naturally occurring gene system in the sense of being manufactured using known techniques of polynucleotide synthesis from sequence data relating to a naturally occurring gene system. Alterations of the sequence may be made which do not alter the function of the dominant control region.

Preferably, the naturally occurring gene system from which the dominant control region is derived or with which it corresponds is a system which exhibits a highly host cell-type restricted expression characteristic preferably at a high level. Specific examples of such systems are the haemoglobin systems such as β-globin system and lymphocyte systems such as the CD2 system.

The dominant control region may consist of, be derived from, or correspond to one or more DNase I super hypersensitive site, preferably of any gene system capable of cell specific expression. Other sequences might however exhibit the functional characteristics of a dominant control region. Where the naturally occurring dominant control region comprises two or more subsequences separated by an intervening polynucleotide sequence or sequences the dominant control region may comprise two or more of the subsequences linked in the absence of all or a part of one or more of the intervening sequences. Thus, if the dominant control region of a naturally occurring gene locus comprises two or more discrete subsequences separated by intervening non functional sequences, (for example, two or more super hypersensitive sites) the vector of the invention may comprise a dominant control region comprising two or more of the subsequences linked together with all or part of the intervening sequences removed.

The DCR may be derived from the β-globin gene locus. As discussed in WO 89/01517, the β-globin gene locus contains a number of DNase I super hypersensitive sites which constitute the DCR. Preferably the dominant control region contains one or more of the DNase I super hypersensitive sites identified within the β-globin locus. Preferably these are from the 5' boundary of the locus, optionally with the 3' boundary sequences. The dominant control region is within a fragment of 21 kb from −1 kb ClaI to −22 kb BglII immediately upstream of the epsilon-globin gene in the β-globin locus. This region contains four DNase I super hyprsensitive sites with intervening polynucleotides (five distinct sites of which two are very close together). Preferably some or all the intervening nucleotides are removed using known techniques such as digestion with exonuclease.

A reduced form of the β-globin locus dominant control region has been produced which exhibits a significantly increased level of expression of a linked gene expression system. This was produced (see WO 89/01517) by ligating the following four fragments.

2.1 kb XbaI - XbaI
1.9 kb HindIII - HindIII
1.5 kb KpnI - BglII
1.1 kb partial SacI fragment This dominant control region, known as a "micro locus", is a 6.5 kb fragment which may be used as a "cassette" to activate a specific gene expression system.

The dominant control region may be derived from CD2 gene locus. The CD2 gene locus contains three super hypersentive sites, one at the 5' boundary of the locus and two at the 3' boundary of the locus. Preferably the dominant control region contains one or more of the DNase I super hypersensitive sites within the CD2 locus. Most preferably, the dominant control region contains both the super hypersensitive sites from the 3' boundary of the locus, optionally with all or a part of any intervening sequence deleted. The dominant control region is contained within a 5.5 kb BamHI to XbaI fragment 3' to the CD2 gene.

In an embodiment of particular interest, a vector according to the present invention comprises a promoter, a dominant control region, a cDNA sequence which codes for a desired polypeptide, and a DNA sequence which is coupled to said cDNA sequence such that hybrid mRNA is produced which is more stable in the host than mRNA from the cDNA alone.

Examples of the various sequences are those mentioned above.

As mentioned above, the DNA sequences may be coupled directly or indirectly.

The present invention also includes a method of producing a polypeptide, which method comprises culturing the expression system of the present invention. Thus the host will be cultivated under the appropriate conditions necessary for growth of the host.

As mentioned above, the expression systems or hosts (and hence vectors) of the present invention may be used to obtain secretion of polypeptides.

Thus the present invention also provides a vector for use in preparing a polypeptide in a mammalian host such that the polypeptide is secreted from the host cells, said vector comprising a promoter, a dominant control region and a gene coding for a desired polypeptide, provided that said gene is not the human β-globin gene.

The promoter and dominant control region or DCR may have any of the definitions given above. Also, the term "vector" and the optional additional sequences are as defined above.

The vector may be used to obtain secretion of a polypeptide from a mammalian host.

In the second aspect of the present invention the gene may comprise any DNA sequence which is capable of being expressed so produce a polypeptide which is capbable of being secreted from the host cells.

Thus the present invention also provides a method of preparing a polypeptide which comprises culturing an expression system which comprises a mammalian host transformed with a vector as defined in the second aspect of the present invention so as to produce polypeptide which is secreted from the host.

In a further aspect of the present invention there is provided a method of producing a polypeptide in a mammalian host, for example erythroid cells, in which the polypeptide is secreted from the host cells.

In general the secreted polypeptide will be harvested by standard techniques known to those skilled in the art and may, if required, be further processed or purified.

The host may include a vector as defined above.

The host may comprise a host as defined above. In general it is preferred that the host comprises erythroid cells, particularly erythroleukaemia cells (for example mouse erythroleukaemia cells).

There is also provided a process for preparing a vector of the present invention (as hereinbefore defined).

The present invention also provides a process for the preparation of a host of the present invention, which process comprises transforming a transfecting a mammalian host with a vector of the present invention.

The vector may be transfected into a population of host cells by any one of a number of transfection methods which result in the integration of at least one copy (but preferably multiple copies) of the expression vector into the host geonome (in a functional form). After transfection, the cells are cultured for a time to allow the integration of the expression vector DNA and the expression of the selectable marker gene. The population of cells is then subjected to a sufficiently high concentration of a toxic substance, that the selectable marker protects against, to kill cells which have not stably integrated the expression vector DNA. Finally, clones of cells which express high levels of the RNA of the product gene or high levels of the product itself are selected by any of a number of available methods which are well known to those skilled in the art.

As mentioned above, the mammalian host cell may be any mammalian host cell which is able to take up a vector of the present invention. Thus the host cell may comprise a cell of a living human or animal, and in particular may comprise a cell of a transgenic animal such as a mouse. Therefore the present invention also provides a transgenic animal transferred with a vector of the present invention (as defined in the first or second aspect of the present invention).

The expression systems (or transformed hosts) of the present invention may be used to produce a desired polypeptide in vitro or in vivo. Thus the present invention also provides a method of gene therapy comprising removing stem cells from the body of an animal, killing stem cells remaining in the body, transforming the cells which were removed with a vector of the present invention (as defined in the first aspect or the second aspect of the present invention) which contains a DNA sequence which codes for a polypeptide which is required by the animal, and replacing the transformed stem cells in the animal body.

Thus this method of gene therapy may be used to replace or supplement a gene different in an animal.

A suitable source of stem cells is bone marrow, and it is referable that it contains both lymphocytes and erythroid stem cells.

It will be appreciated that the host cells of the present invention may contain more than one copy of a vector of the present invention, that is of a vector of the first aspect or second aspect of the present invention. Host cells containing multiple copies of the expression vector DNA may be generated by two or more successive rounds of transfection and selection (using a different selectable marker for each round) or by subjecting a population of cells, produced as described above, to a conventional amplification protocol to increase the copy number of the integrated expression vector DNA.

The expression system/vectors of the present invention may be used to prepare heterologous polypeptides, and in particular polypeptides which possess useful pharmacological properties. Examples of such polypeptides include, for example, GCSF, hGH and PLA2.

The present invention has numerous advantages over prior art and generally avoids many of the problems associated with these methods.

In general, the present invention provides expression systems/vectors which may be produced relatively rapidly, and which give high expression levels of the desired RNA and polypeptide. Also, in general, the present invention provides novel recombinant host cells with very high expression levels of the desired polypeptide. Generally, the methods of the present invention are applicable to any eukaryotic host cell for which a DCR sequence is described or in which a DCR sequence is active or can be made to be active.

In particular, DCR elements have been used in combination with erythroid cell types (mouse erythroleukaemia [MEL], rat erythroleukaemia [REL] or human erythroleulaemia [HEL] cells) and it has been found that these cells secrete heterologous proteins with surprising efficiency. Novel expression systems have been produced which are capable of high-level, prolonged secretion of heterologous proteins. These expression systems can be used for small or large scale culture and secretion in vitro and the same vectors can be used for in vivo protein production either for production of recombinant protein or as part of gene therapy protocols. This system can efficiently deliver proteins (of therapeutic value) into the bloodstream of mammals which carry the vector.

DESCRIPTION OF THE FIGURES

FIG. 4: Construction of HGH cDNA.

```
5' AGC TTG AAT TCC CCG GGT CTA GAG CGG CCG CCT CGA GGG ATC CCT GCA GGT
3'     AC TTA AGG GGC CCA GAT CTC GCC GGC GGA GCT CCC TAG GGA CGT CCA

ACC ATC GAT GAG CT 3'
    TGG TAG CTA C     5'
```

Figure 15:
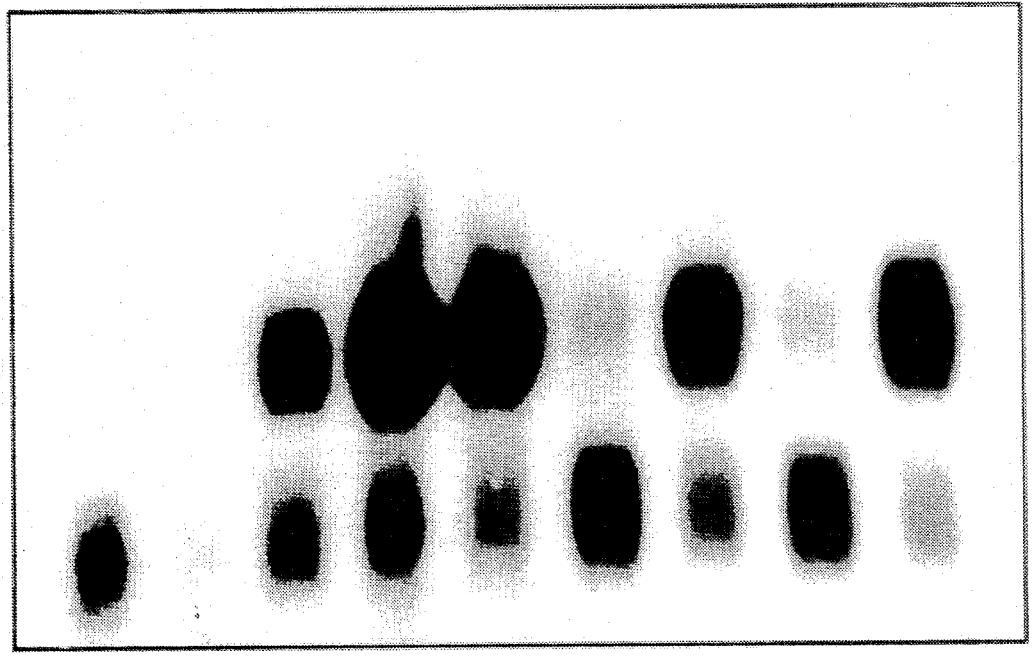

FIG. 15: Northern blot analysis of major basic protein expression. In this Figure (i) indicates major basic protein, (ii) indicates globin, PP=pooled populations, and a, b, a, c, e and f=individula clones.

Figure 16:
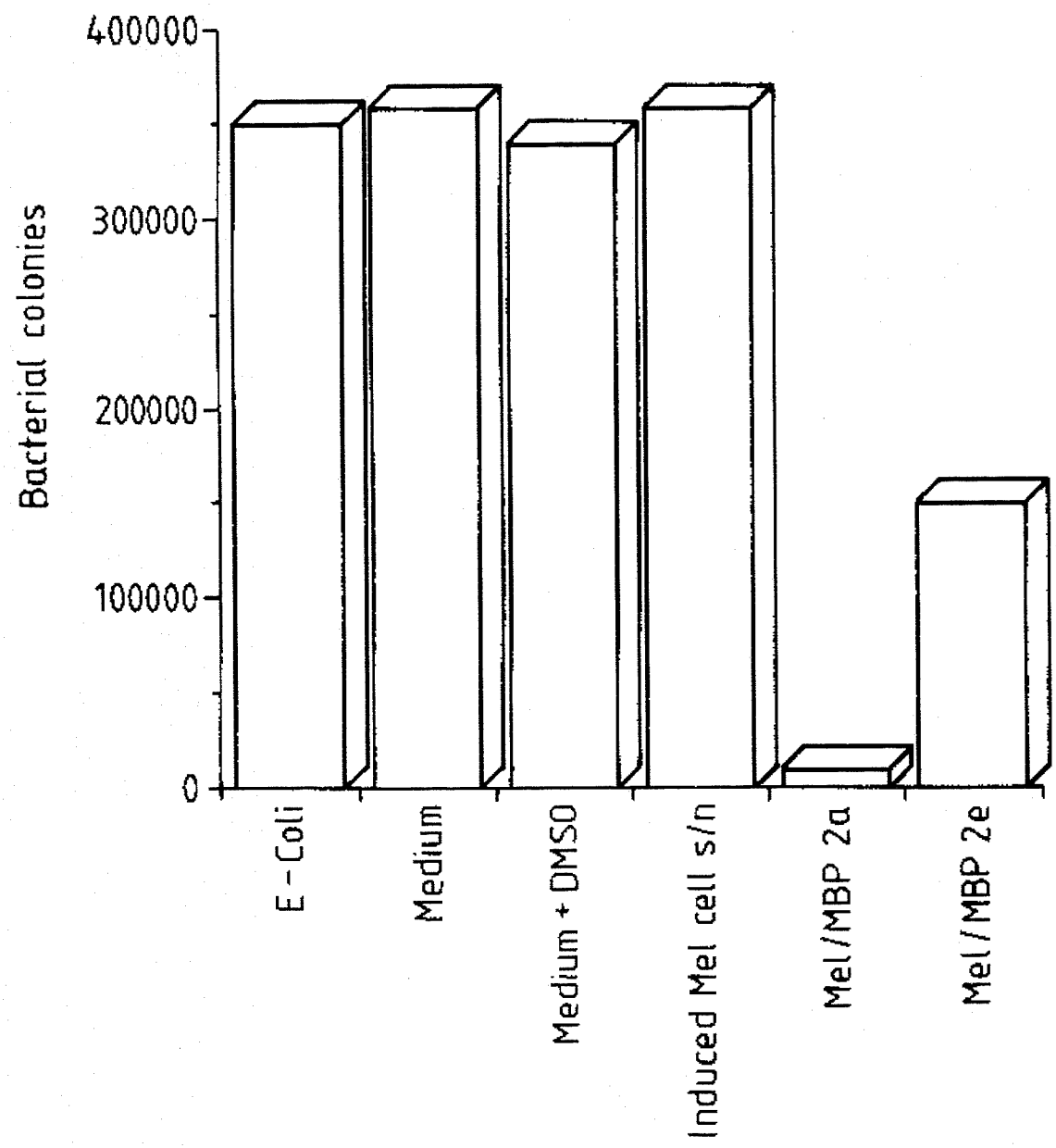

FIG. 16: Illustrates E. coli killing assay results.

Figure 17:
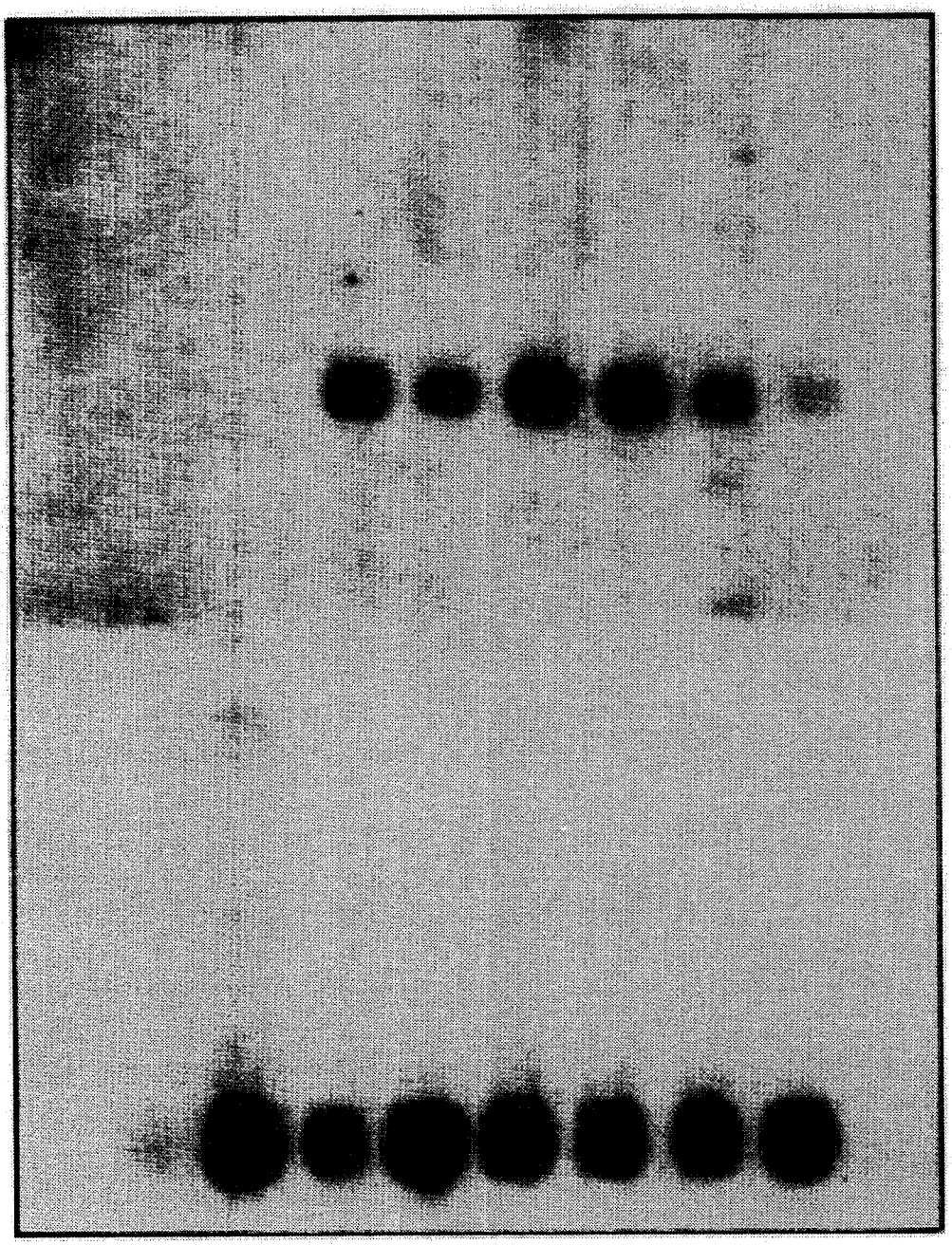

FIG. 17: Northern blot analysis of TNFα Receptor expression. In this Figure (i) indicates TNFα receptor, (ii) indicates mouse globin, U=uninduced, I=induced, and 1,2, 3,4 and 5 are individual clones.

Figure 18:
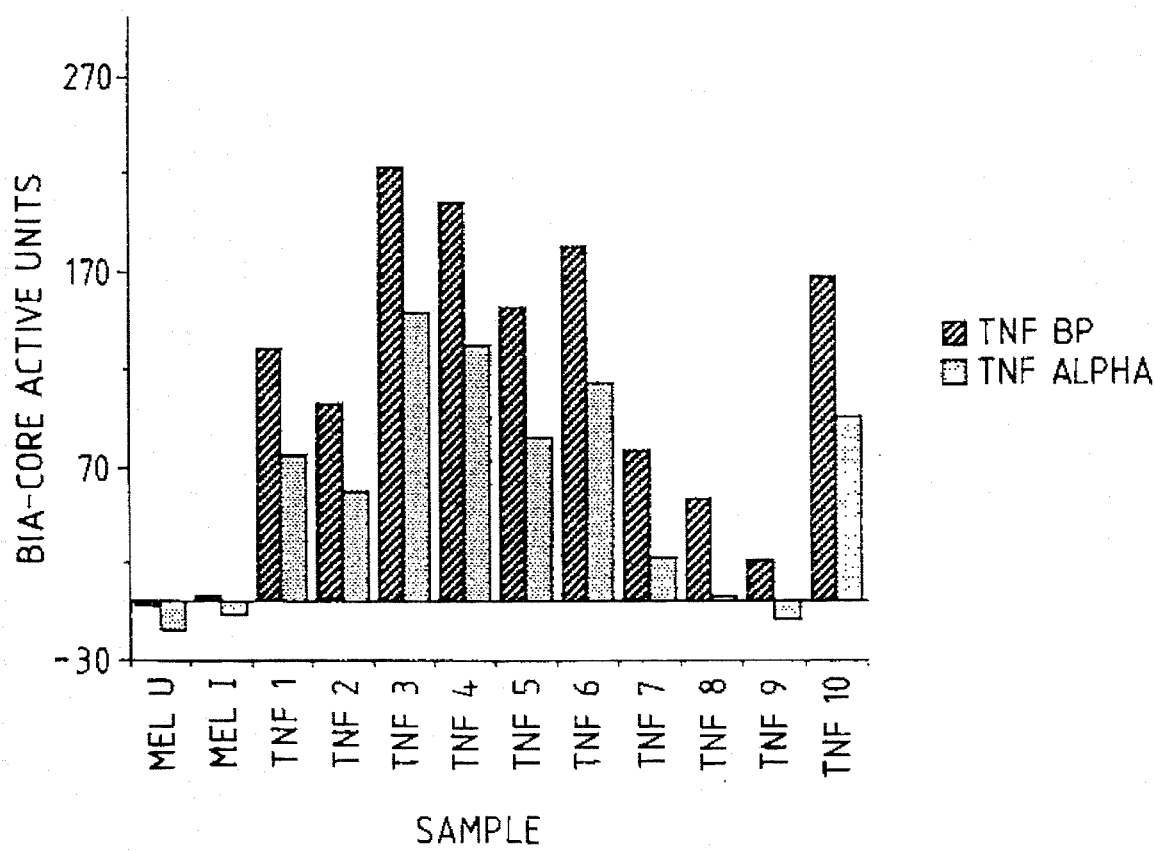

FIG. 18: Illustrates TNFα receptor expression.

Figure 19:
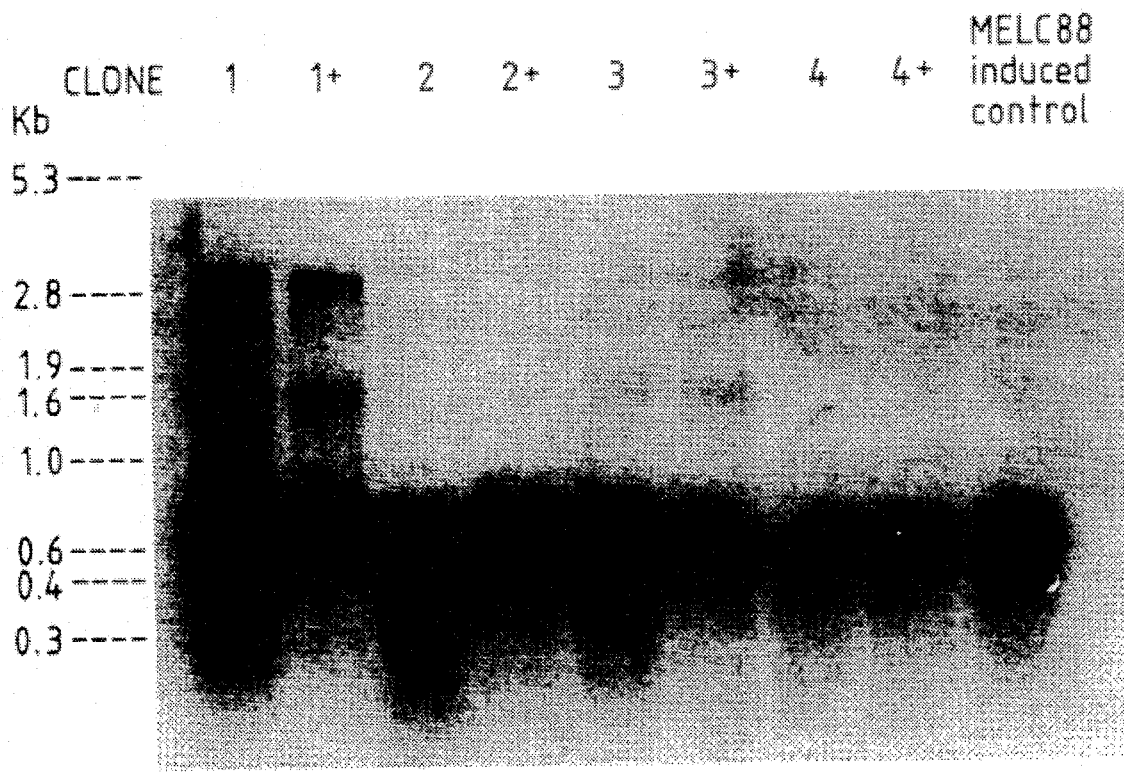
Figure 19:
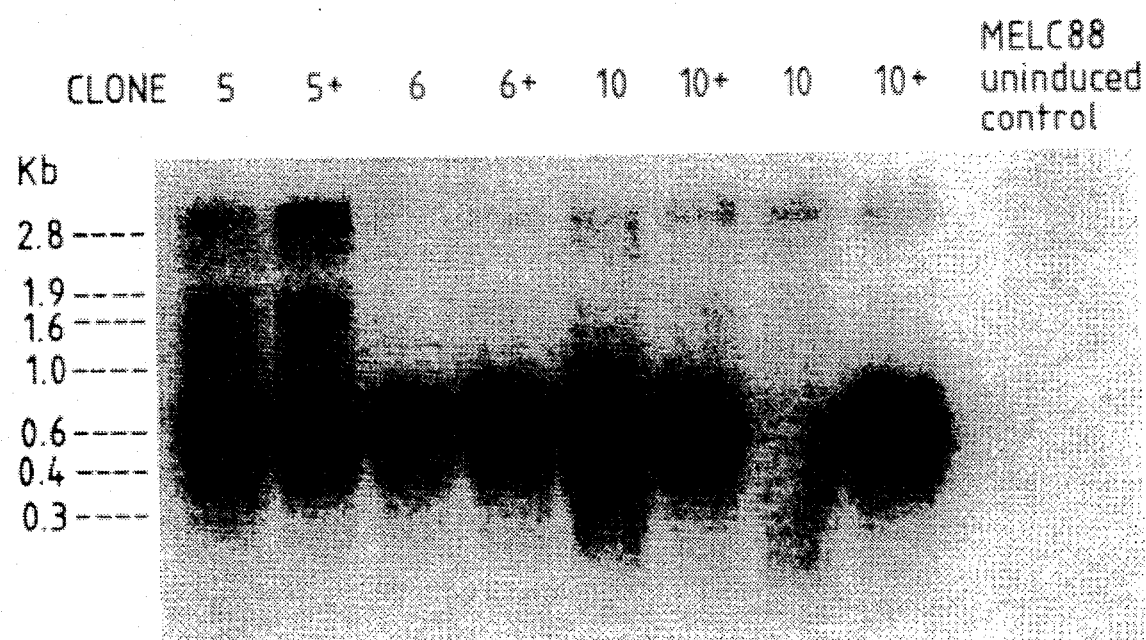

FIG. 19: Northern blot analysis of hNK-2 receptor transfected Mel cells probed with murine β-globin exon 2 fragment. In this FI6G. 30=induced in the presence of an antagonist of hNK-2R.

Figure 20:
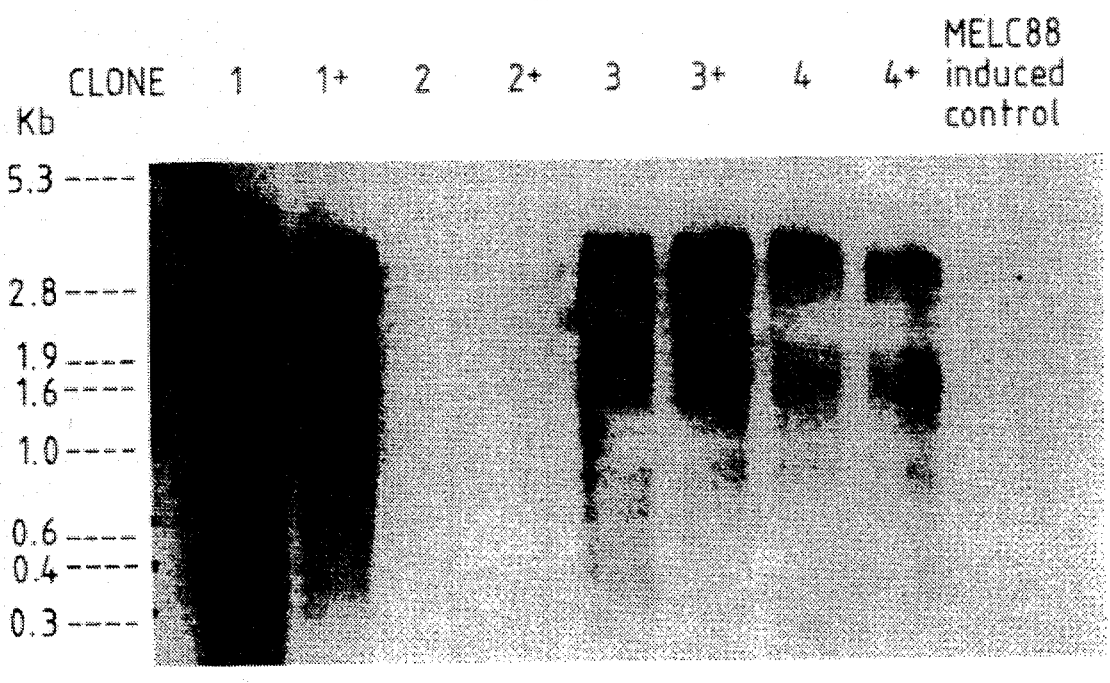
Figure 20:
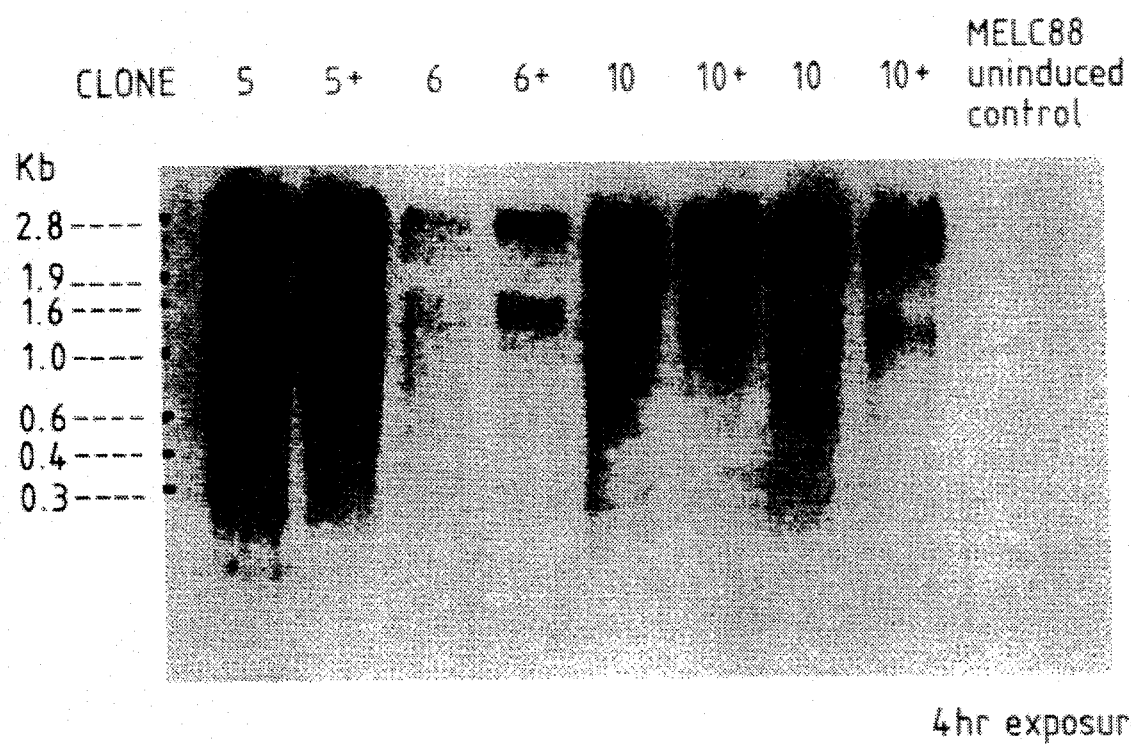

FIG. 20: Northern blot analysis of hNK-2 receptor transfected Mel cells probed with hNK-2R cDNA. In this Figure +=induced in the presence of an antagonist of hNK-2R.

Figure 21:
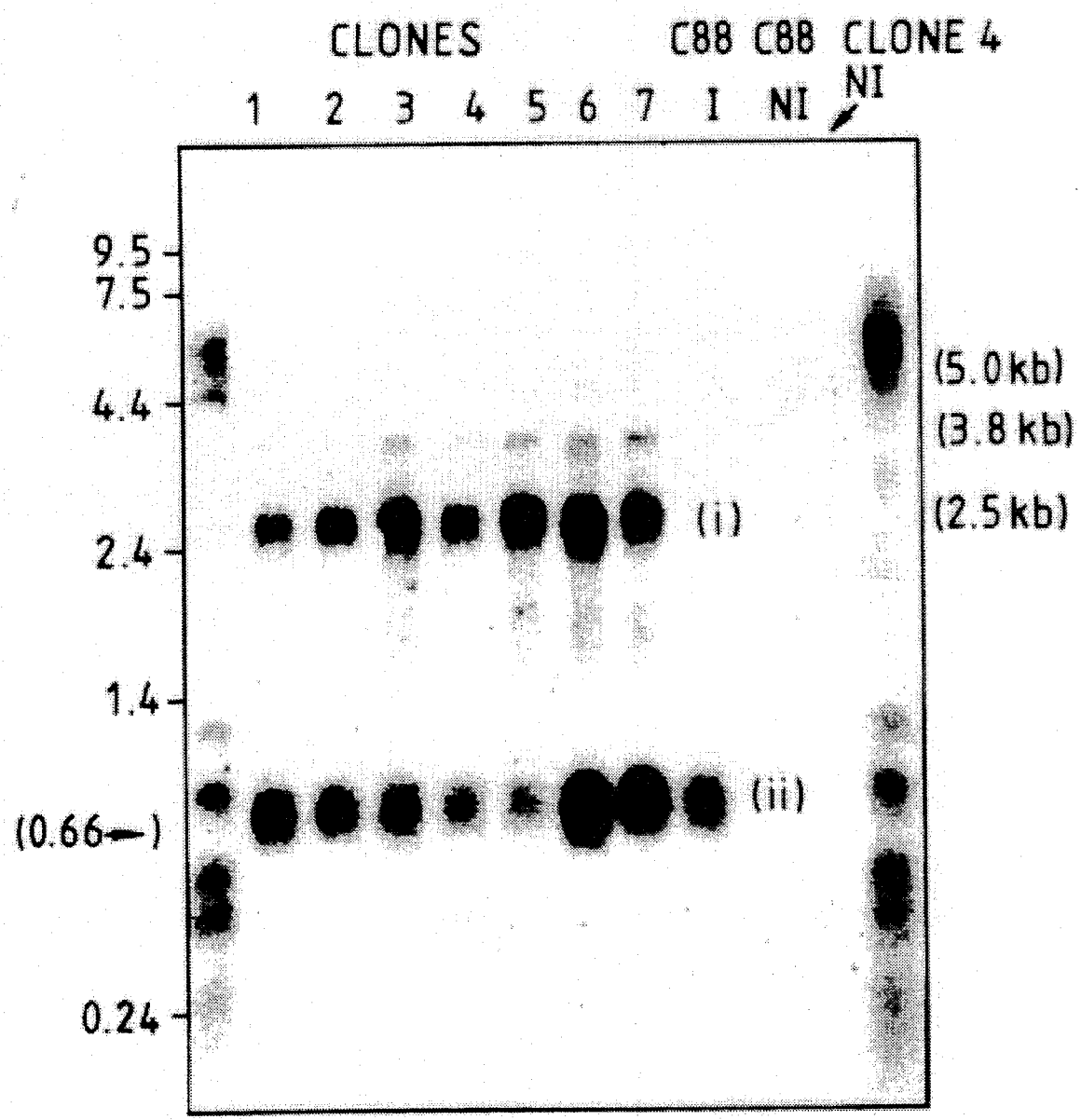

FIG. 21: Northern blot analysis of human serum albumen expression. In this Figure, (i) indicates human serum albumen, (ii) indicates globin, I=induced, NI=non-induced, and 1,2,3,4,5, and 6 are individual clones.

Figure 22:
Figure 22:
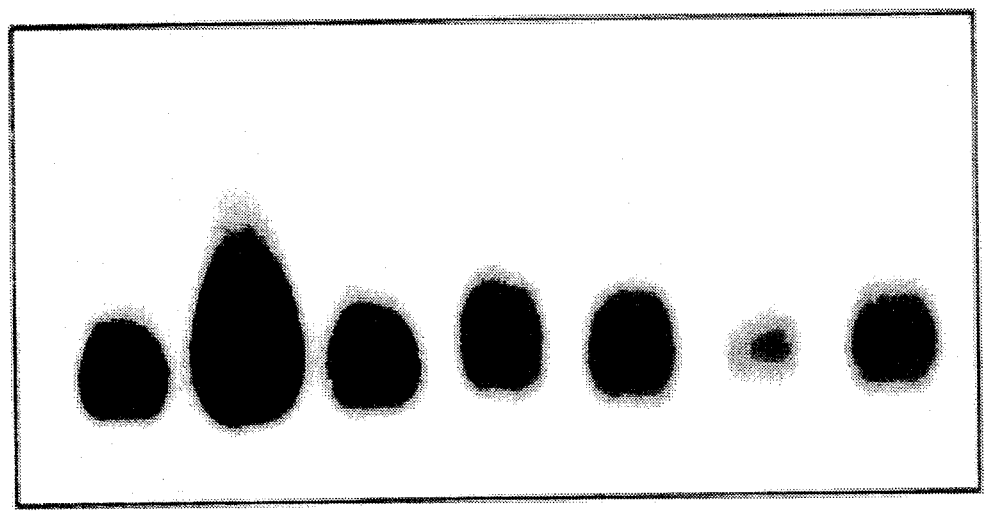
Figure 23:
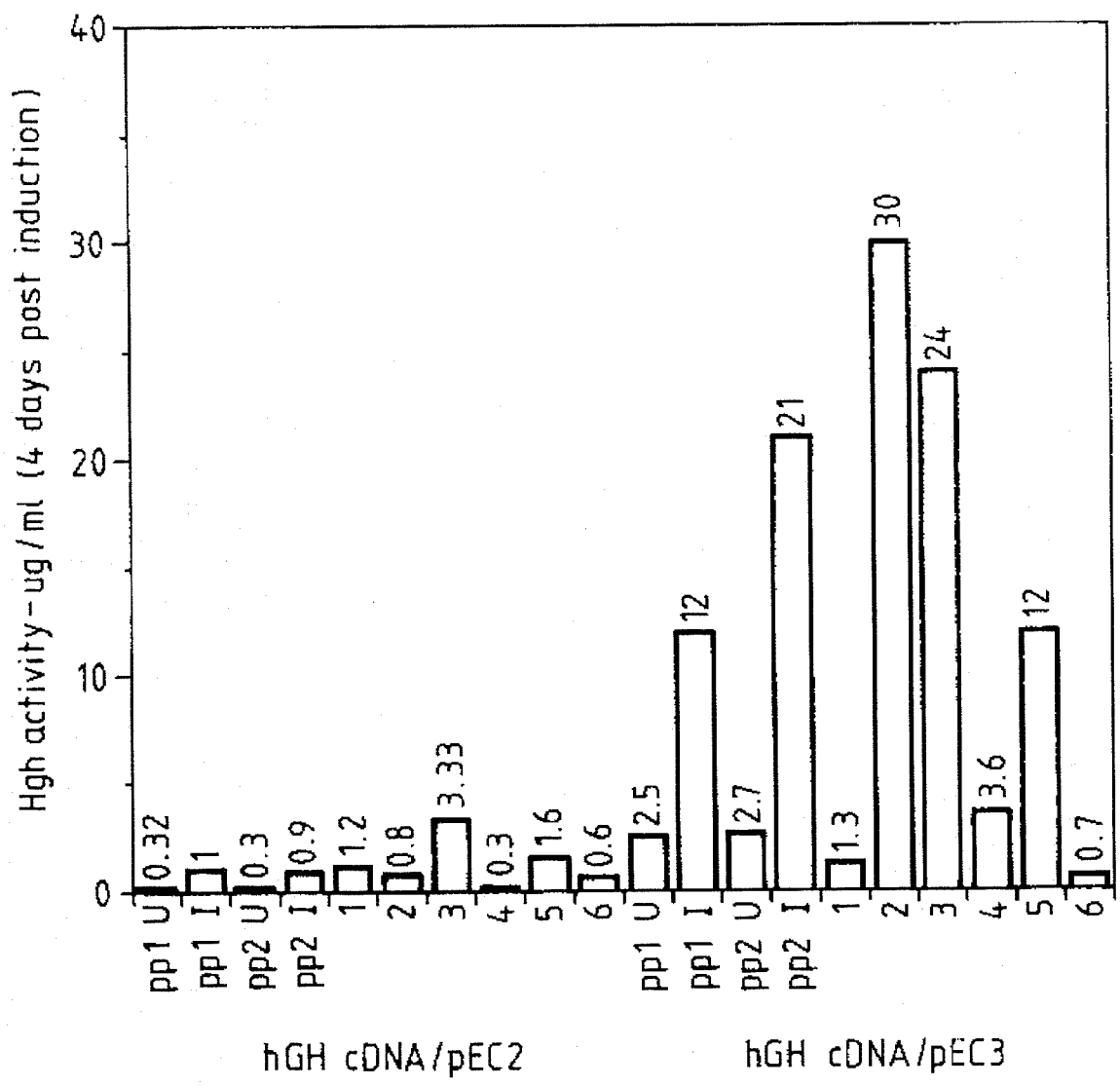

FIG. 22: Northern blot analysis of hGH expression. In this Figure, (a) indicates hGH RNA, (b) indicates mouse globin, U=uninduced, I=induced, 1b, 1c, 1d, 2a, 2c, 2f are individual clones. FIG. 23: Comparison of hGH/EC2 and hGH/EC3 in Mel cells. In this Figure PP=pooled populations, U=uninduced, I=induced, and 1,2,3,4,5 and 6 are individual clones.

DETAILED DESCRIPTION

A) CONSTRUCTION OF VECTOR DNAs

The final expression vectors were constructed (for convenience) from two intermediate plasmids. One plasmid (pGSE1417) contains the DCR sequences and a selectable marker gene and the second plasmid (derived from pUNIVEC) contains the expression cassette of choice. The plasmids were made as described below:

Construction of plasmid pGSE1417

This plasmid (see FIG. 1C), which contains the β-globin DCR microlocus is exactly as described by Talbot et al, nature, 338, 1989; see also collis et al, embo journal, vol 9, no. 1, 233–240, 1990.

Construction of plasmid pUNIVEC (also referred to herein as pEC₂)

Figure 1A:
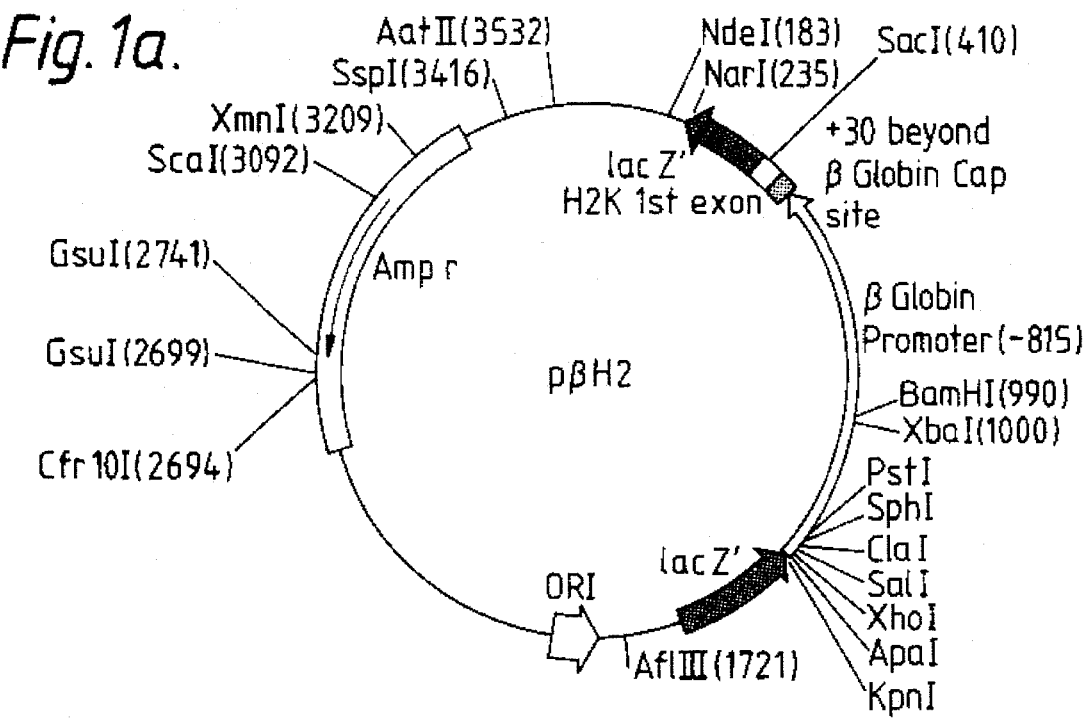
FIG. 1: Plasmid maps of plasmids pβH2, pβ-mini and pGSE1417.
Figure 1B:
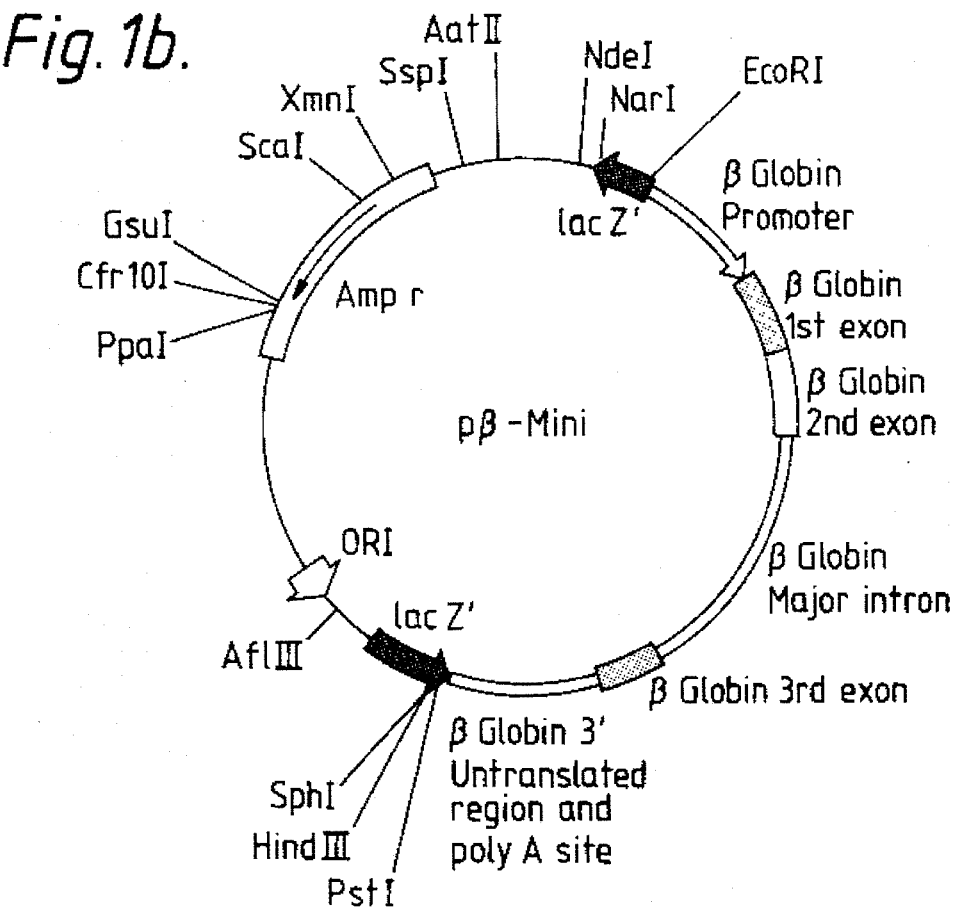
Figure 1C:
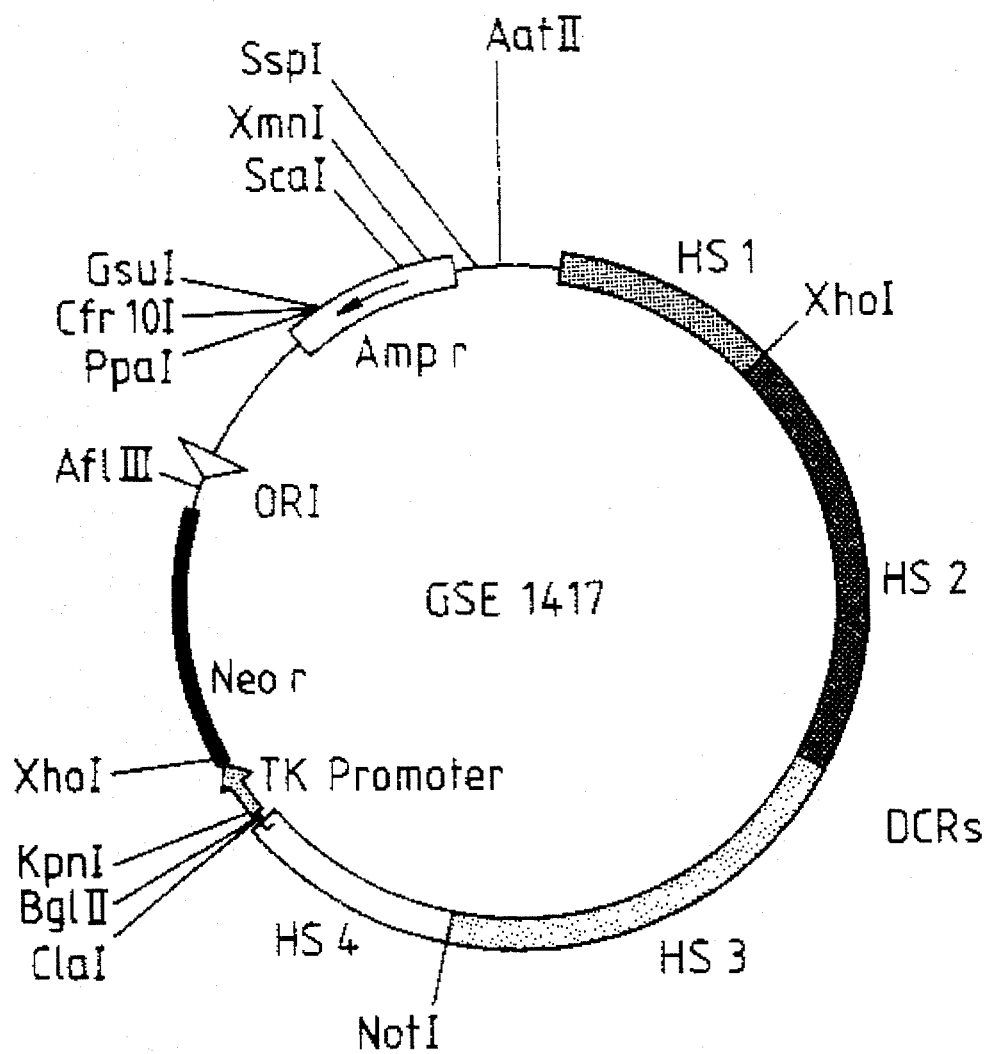
Figure 2:
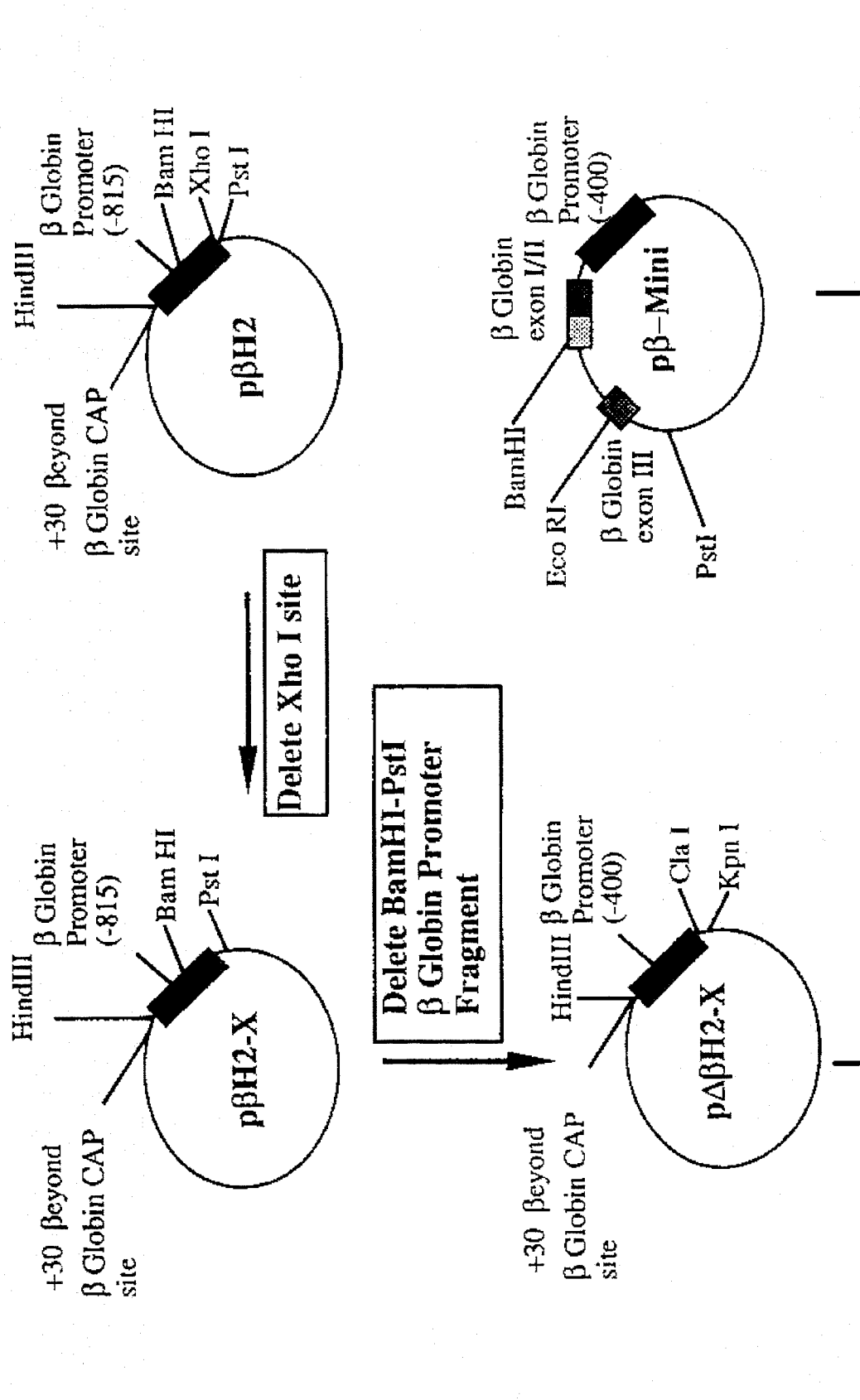
FIG. 2: Construction of plasmid pUNIVEC.
Figure 2:
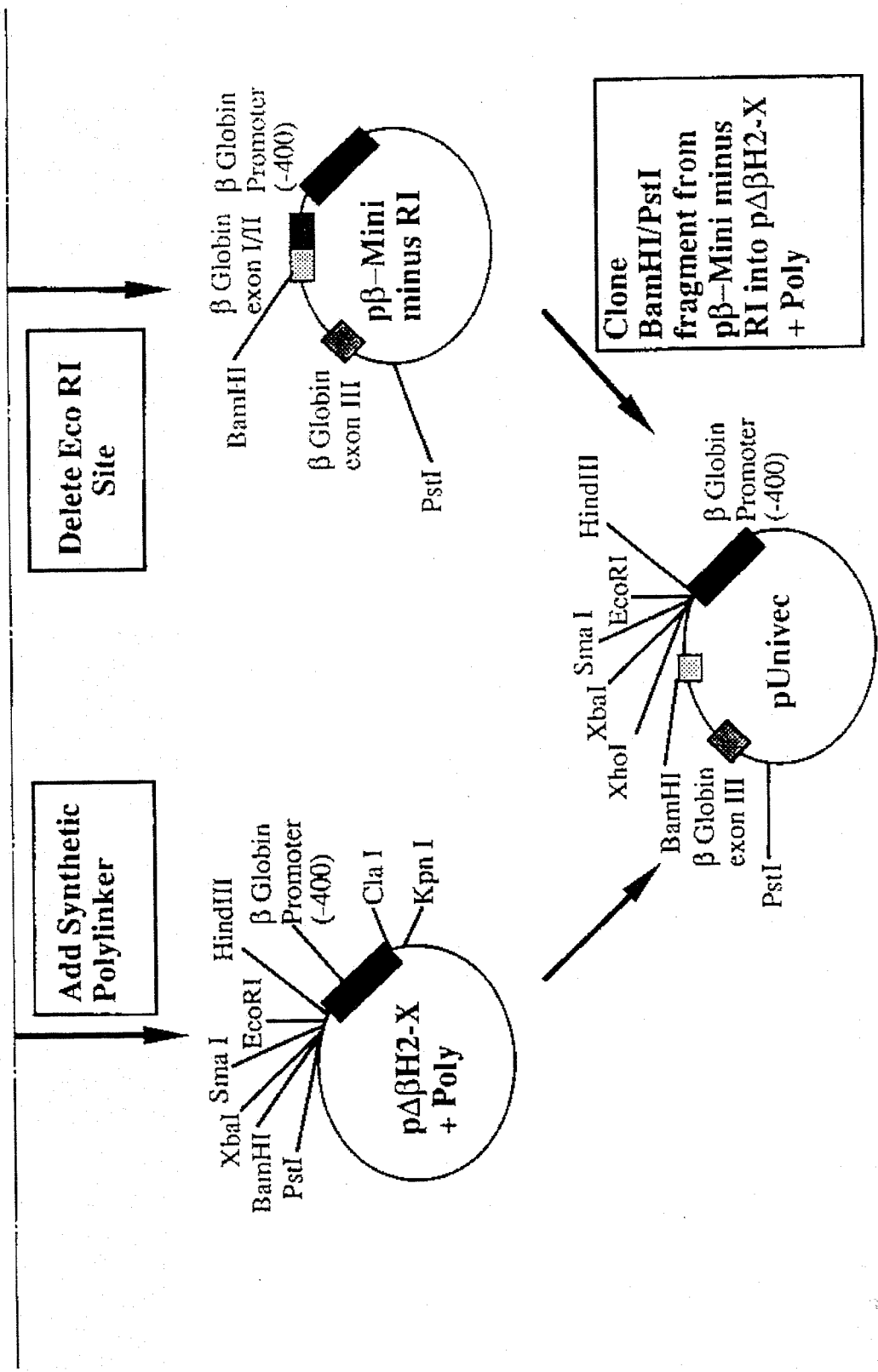
Figure 3:
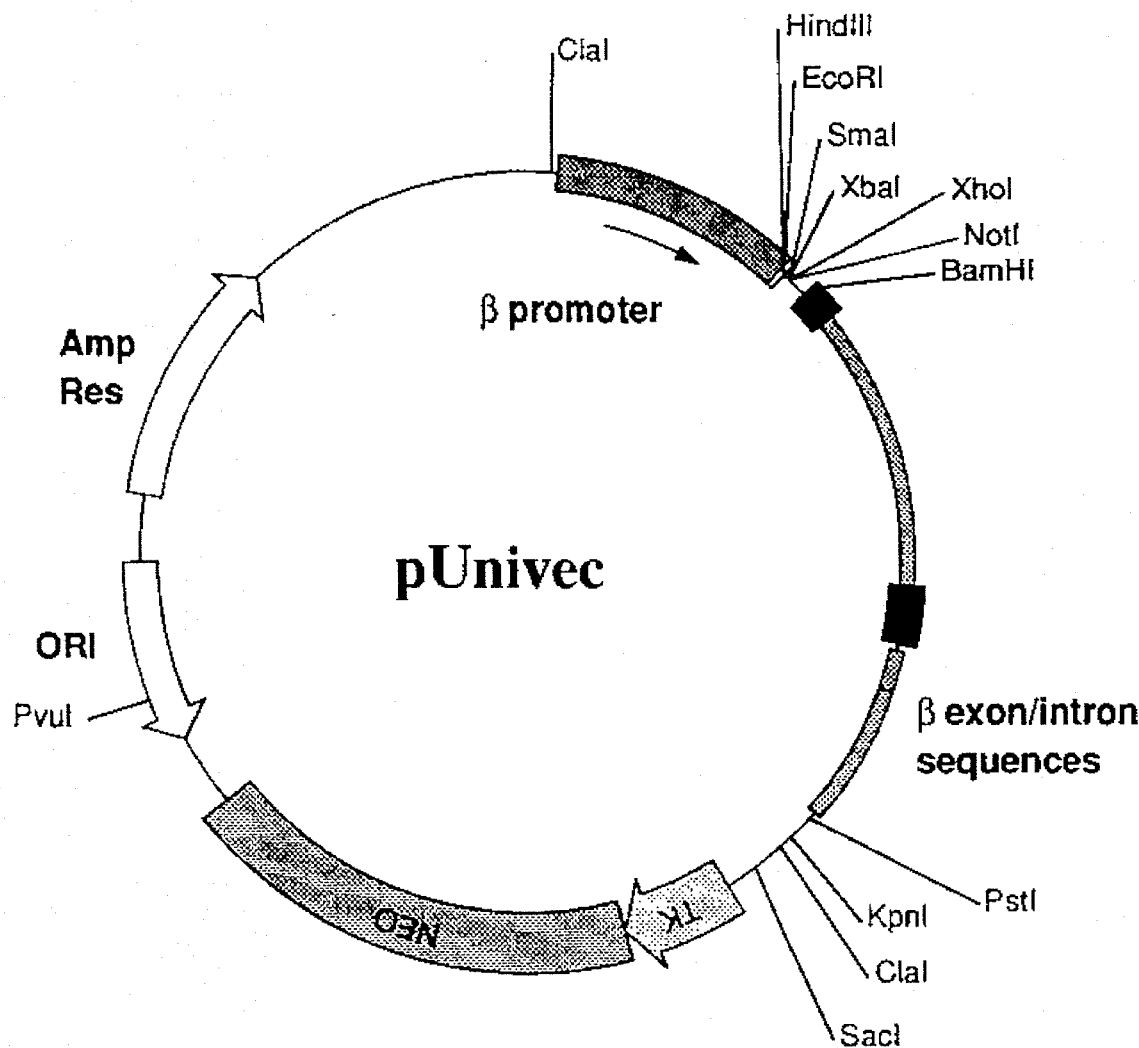
FIG. 3: Plasmid map of pUNIVEC (pEC$_2$).

Starting with plasmid pβH2 (containing the human β-globin promoter from –800 to +30 and the first exon of the murine H2K gene, in a pBLUESCRIPT backbone; see FIG. 1A), the XhoI site 5' to the β-globin promoter was removed to generate plasmid pβH2-X. The β-globin promoter was then shortened to approx –400 by PstI+BamHI restriction digestion to give plasmid pΔβH2-X. The H2K gene was then removed by HindIII+SstI restriction digestion and replaced with a synthetic polylinker oligonucleotide as below (SEQ ID NO:1 and SEQ ID NO:2.

which contains the recognition sequences for HindIII, EcoRI, SmaI, XbaI, NotI, XhoI, BamHI, PstI, KpnI, ClaI and SstI restriction endonucleases. This resulted in the plasmid pΔβt2-X+Poly (also referred to as pEC¹). To complete the vector pUNIVEC (pEC₂), a fragment of the human β-globin gene from the natural BamHI site in exon 2 to the PstI site downstream (3') of this, encompassing exon 3 and the polyadenylation site, was removed from plasmid pβ-mini (FIG. 1B) and cloned into pΔβH2-X+Poly between the BamHI and PstI sites of the polylinker. FIG. 2 outlines the steps involved in the production of pUNIVEC.

Construction of expression vectors

Figure 4A:
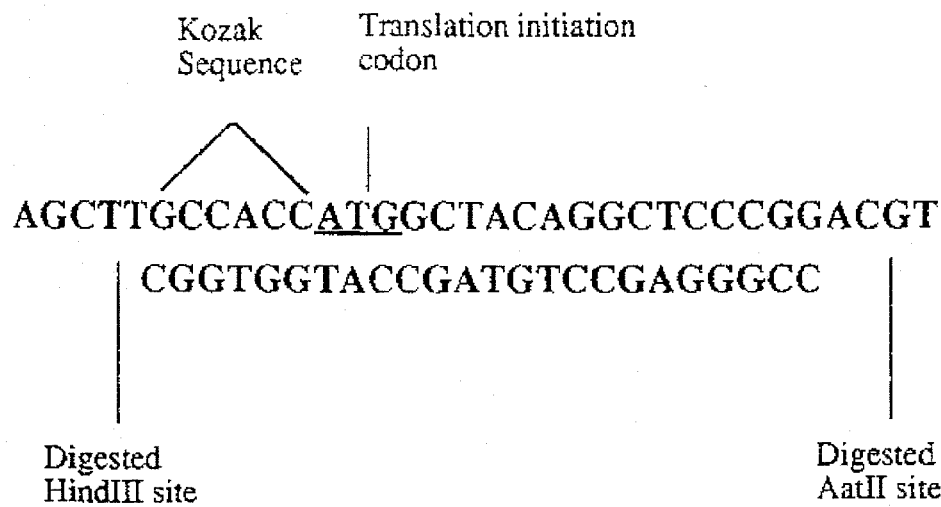
FIG. 4a illustrates the sequence of oligonucleotide used to re-build the 5' end of HGH cDNA (See SEQ ID NO:5 and SEQ ID NO:6)
Figure 4B:
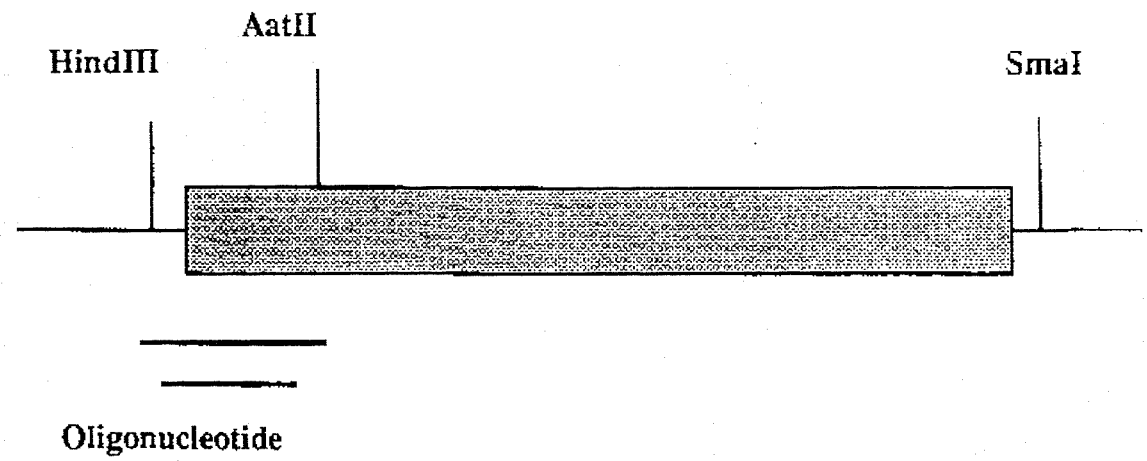
FIG. 4b illustrates the insertion of the oligonucleotide into the 5' end of HGH cDNA.

Essentially, all cDNA expression vectors were constructed the same way. The cDNA (eg human growth hormone) was cloned into the polylinker of pUNIVEC with the translational start site nearest to the β-globin promoter. The expression cassette (β-globin promoter+cDNA+β-globin intron/exon sequences and polyadenylation sequences) were then transferred into the vector pGSE1417 (usually as a ClaI-KpnI fragment into the unique ClaI and KpnI sites of pGSE1417) such that the β-globin promoter was nearest the DCR sequences and that the expression cassette was located between the DCR sequences and the selectable marker (tk-neo) gene. FIG. 4 shows the construction of the final expression vector for the human growth hormone (HGH) cDNA.

For the expression of heterologous proteins from genomic sequences, the genes (including their natural polyadenylation sequences) were cloned into a precursor of pUNIVEC called pΔβH2-X+Poly (pEC₁) (see FIG. 2) which lacks the human β-globin intron/exon sequences and the β-globin polyadenylation sequence.

B) TRANSFECTION AND SELECTION

Cell lines

In the examples below, mouse erythroleukaemic cell lines (MEL) were used. Production and characteristics of MEL cells are known to those skilled in the art and are descibed by Deisseroth et al, Proceedings of the National Academy of Sciences, Volume 72, No. 3, p1102–1106; and by Friend et al, Proceedings of the National Academy of Sciences, Volume 68, p378–382, 1971. The examples below refer to MELC88 and 11A21 mouse erythroleukaemic cell lines, but the precise cell line is not critical and any mouse erythroleukaemic cell line in the appropriate period of differentiation may be used in the following Examples. The globin DCRs are active in erythroid cells and the MELC88 and 11A21 cells were induced to differentiate and become erythroid in order to see the full activity of the DCR sequences.

Media

All stock cell lines were grown in non-selective media, either (A) Dulbecco's minimal essential medium (DMEM, Flow labs; liquid media with sodium bicarbonate) supplemented with 2 mM glutamine (Flow Labs), 10% foetal calf serum (1% for 11A21) and penicillin/streptomycin antibiotics (Flow Labs) or in (B) α-MEM (Flow Labs; liquid media) supplemented as above. Transfected cell lines were maintained in the above media with the aminoglycoside geneticin sulphate (G418; Gibco-BRL Cat No 066-1811) added to 1 mg/ml final concentration or with hygromycin-B (Boehringer Mannheim) at 0.8 mg/ml final concentration (or occasionally with both antibiotics). Transfectant lines were selected as described below.

Linearisation of expression plasmids

In order to introduce the expression plasmids into cells, they were first linearised by digestion with a restriction enzyme which cuts at a single site within the plasmid and which does not interfere with the transcription of the gene of interest or the selectable marker gene in mammalian cells. This was PvuI for most plasmids, including pDCR/NEO/HGHcDNA and pDCR/NEO/HGHgenomic.

Electroporation of cells

The MEL cells were harvested while growing exponentially, washed twice in electroshock buffer (140 mM NaCl, 25 mM HEPES pH7.5, 0.75 mM $Na_2HPO_4$) and then resuspended at a density of $10^7$ cells/ml in fresh (ice cold) electroshock buffer. One ml of cell suspension ($10^7$ cells) were added to the linearised plasmid DNA (typically 10→100 µg of DNA in digestion buffer, water or 10 mM TRIS, 1 mM EDTA pH8.0) in an electroporation chamber (Bio-Rad Gene Pulser cuvette; 0.4 cm path length) and incubated on ice for 5–10 minutes. The cell-DNA mixture was then pulsed at 250 V using a Bio-Rad Gene Pulser electroporator at a capacitance of 960 µF. The cells were allowed to stand for 5–10 minutes at room temperature and then were resuspended in non-selective growth medium followed by plating in 24-well tissue culture plates at densities of $10^5$ original cells/well (1 plate) and $10^4$ original cells/well (1 plate). After 20–30 hours, an equal volume of selective medium (typically 1 ml) containing G418 at 2 mg/ml (or hygromycin-B at 1.6 mg/ml where appropriate) was added to each well. The resulting cell suspensions (in 1x selective media) were incubated at 37° C. in tissue culture incubators with 5–10% $CO_2$.

Electroporated cell suspensions were incubated at 37° C. for 7–14 days until individual clones of drug-resistant cells could be seen. These were then picked (using a pasteur pipette or a Gilson Piperman semi-automatic pipettor) individually or in pools and expanded in selective media.

Calcium Phosphate mediated transfection of Suspension Cells

The method of Gorman et al (Molecular and Cellular Biology, p1044–1051, 1982) was used throughout and briefly comprises of the following steps. Solution A was made by taking 20 ul of 70 mM sodium phosphate with 1 ml of 2xHBS pH7.1 (10 g/l Hepes, 16 g/l NaCl). Solution B was made by taking 50 µg of the DNA to be transfected in 1 ml water with 120 µl of 2M CaCl2. A 2 ml precipitate was made by adding solution B dropwise to solution A, which was left at room temperature for 20 minutes. Suspension cells which have been maintained in exponential phase for 2–3 days were taken at a cell density of 6–8×$10^5$/ml. The 2 ml precipitate was added to 18 ml of suspension incubated at 37° C. for 4–6 hours. The cells were then washed twice in PBS, counted and then 1 ml was plated at 2×$10^4$/ml and 2×$10^5$/ml in 24 well tissue culture plates. The plates were incubated overnight at 37° C. after which 1 ml/well of 2 mg/ml G418 in culture medium was added. The plates were then left at 37° C. for 7–12 days for colonies to appear.

Lipofection Transfection of Suspension Cells

Suspension cells were maintained in logarythmic phase growth for 2–3 days prior to the transfection such that they were at a density of about 5×$10^5$/ml on the day of the transfection. Transfections were carried out using the Boehringer Mannheim DOTMA reagent, using the method described in the kit which briefly comprised the following steps:

1. 100 µl of the DOTMA dispersion (1 mg/ml) was diluted in 4 ml of tissue culture medium.
2. 0.1–10 µg of DNA was diluted separately in 4 ml of tissue culture medium. The DNA and DOTMA solutions were mixed.
3. The medium was removed from the cells by centrifugation and the DOTMA/DNA mix added to the cells which were then incubated at 37° C. for 3–6 hr at 5–10% $CO_2$.
4. The DOTMA/DNA mix was removed from the cells by centrifugation and replaced with normal growth medium and the cells plated in 24 well plates as above. Selective medium was applied as above.

INDUCTION OF EXPRESSION

Clonal transfectant cell lines or pooled populations were induced to express in the same way. The cells were maintained in exponential growth by daily dilutions in selective media to 2×$10^5$ cells/ml. After 3–4 rounds of daily dilution, the cells were allowed to grow overnight and then dimethylsulphoxide (DMSO) was added to the selective media at a final concentration of 2%. The cells were then kept in this inducing medium for the duration of the experiment.

EXAMPLES

Example 1 - Expression of HGH cDNA

Figure 5:
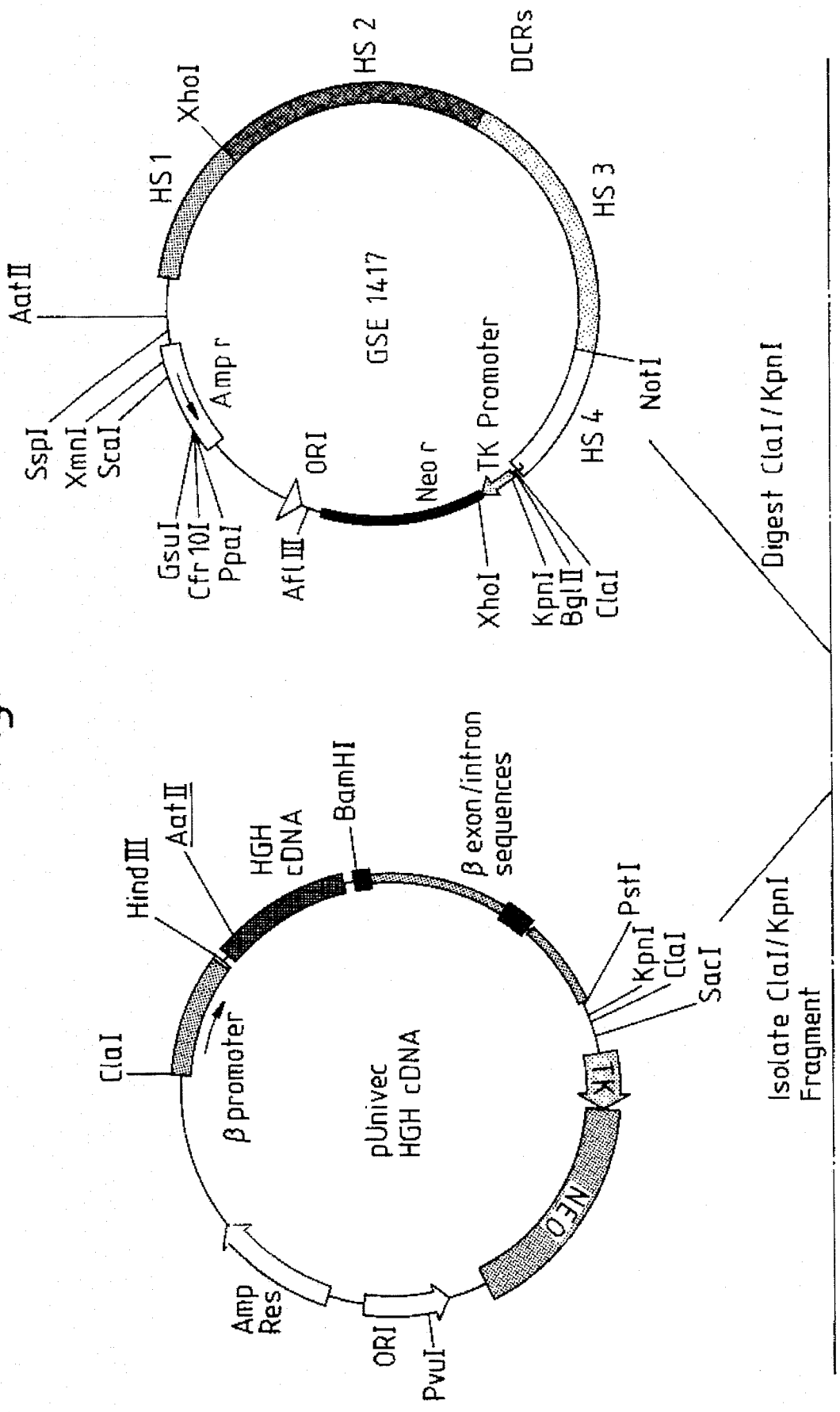
FIG. 5: Construction of the final HGH cDNA expression vector.
Figure 5:
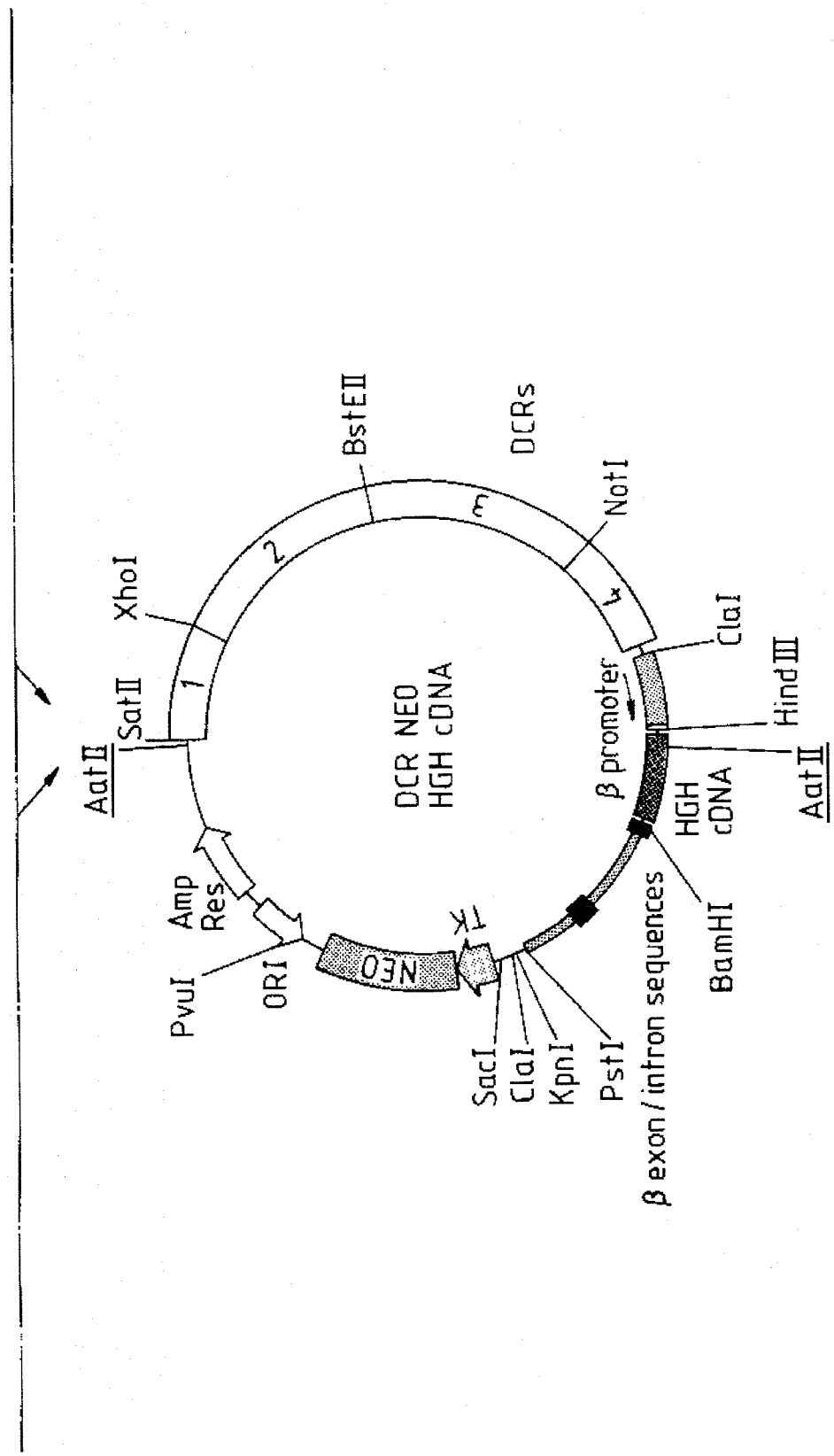

A partial HGH cDNA was obtained from Dr L Hall (Bristol University). This cDNA lacked the natural HGH translational initiation codon. The start of the gene was re-built incorporating a consensus eukaryotic translation initiation site (Kozak et al, Molecular and Cellular Biology, Vol. 7, 3438–3445, 1987) using a synthetic oligonucleotide which spanned from approximately 30 bp upstream (5') of the translational start site (ATG) to the natural AatII restriction endonuclease site near the start of the cDNA (see FIG. 4A and 4B). The complete HGH cDNA from the HindIII site (provided by the synthetic oligonucleotide) to the natural SmaI restriction site was cloned into pBLUESCRIPT. The HGH cDNA sequences, containing the natural HGH secretory signal sequences, were removed from this plasmid as a HindIII to BamHI fragment and cloned into the HindIII and BamHI sites of the intermediate vector pUNIVEC. This plasmid then contained the HGH cDNA expression cassette. This cassette was removed from pUNIVEC by digestion with ClaI and KpnI and was inserted into the ClaI and KpnI sites of pGSE1417 to give the plasmid pDCR/NEO/HGH-cDNA. This is outlined in FIG. 4C. The DNA sequence of the final HGH cDNA used in these experiments is shown in FIG. 5.

Plasmid pDCR/NEO/HGHcDNA was digested with the restriction endonuclease PvuI and then the linear DNA was introduced into MEL C88 cells by electroporation, calcium phosphate mediated transfection or lipofection. Monoclonal transfectant cell lines and pooled populations were selected as described. Each transfectant line was induced to differentiate (and hence express under the control of the erythroid DCR elements) as described and the secreted growth hormone was measured using a commercial RIA kit (Nicholls Institute Tandem-R HGH assay kit). The mRNA levels of the transfectant HGH cDNA were measured by Northern blotting with a HGH cDNA probe using the mouse β-major globin RNA levels as an internal control.

Results - Example 1

The stable cell lines expressed and secreted HGH at high levels. Murine red cells are not known as secretory cells and the level of secretion from the recombinant clones was indeed surprising. Initial HGH assays on cell supernatants and on cell lysates indicated that >95% of the HGH which was produced was secreted into the cell culture medium. Secretion (rather than cell lysis) was confirmed using the fungal inhibitor of secretion, brefeldin-A (see Example 4).

Table 1 gives the levels of secreted HGH which were obtained after four days of induction with the HGH expression vector described above. Pooled populations and monoclonal lines were both measured.

TABLE 1

Secretion of HGH from Transfected MELC88 Cells

| Cell Line | Monoclonal | [HGH] μg/ml |
|---|---|---|
| Electroporation | | |
| PP1 | NO | 1.7 |
| PP2 | NO | 1.9 |
| 1 | YES | 0.8 |
| 2 | YES | 1.5 |
| 3 | YES | 3.5 |
| 4 | YES | 5.0 |
| CaPO$_4$ Transfection | | |
| PP1 | NO | 5.0 |
| PP2 | NO | 3.5 |
| 1 | YES | 2.0 |
| 2 | YES | 12.0 |
| 3 | YES | 4.5 |
| 4 | YES | 50.0 |

Figure 6:
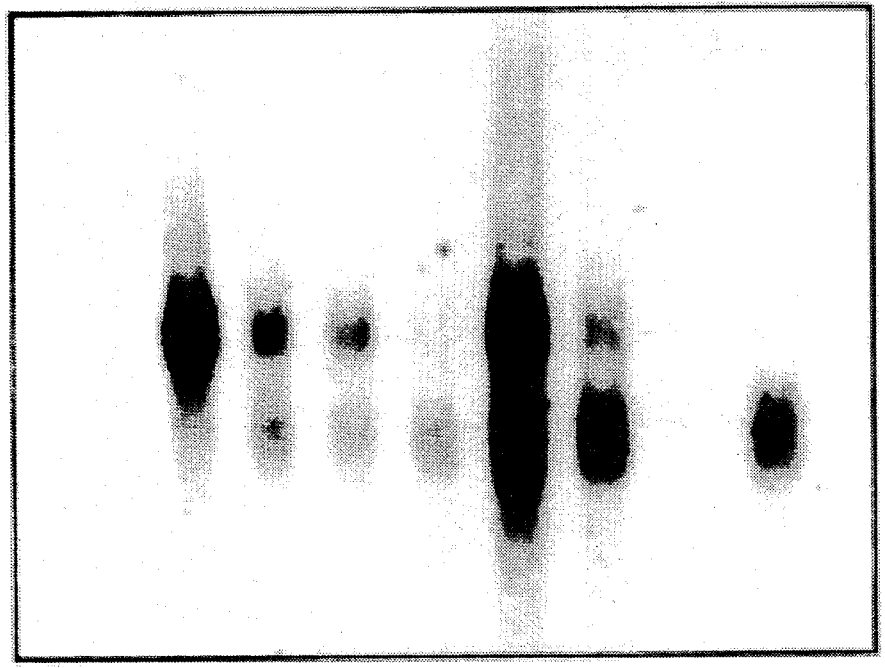
FIG. 6: Northern blot analysis of induced MELC88 clones transfected with the HGH cDNA expression vector. In this Figure (i) indicates human growth hormone, and (ii) indicates mouse β-globin. Lane A=clone 4, lane B=PP1 (pooled population 1), lane C=PP2 (pooled population 2), lane D=clone 1, lane E=clone 2, lane F=clone 3, lane G=MelC88 uninduced, lane H=MelC88 induced.

The expression levels seen are very high in comparison with standard (unamplified) mammalian expression experiments. A Northern blot of the total mRNA from the induced cell lines, probed with a HGH specific probe confirmed that the mRNA levels of the chimaeric globin/HGH RNA (produced from the expression vector) are comparable to the levels of the endogenous mouse β-major globin (see FIG. 6).

Example 2 - Expression of HGH Gene

Figure 7:
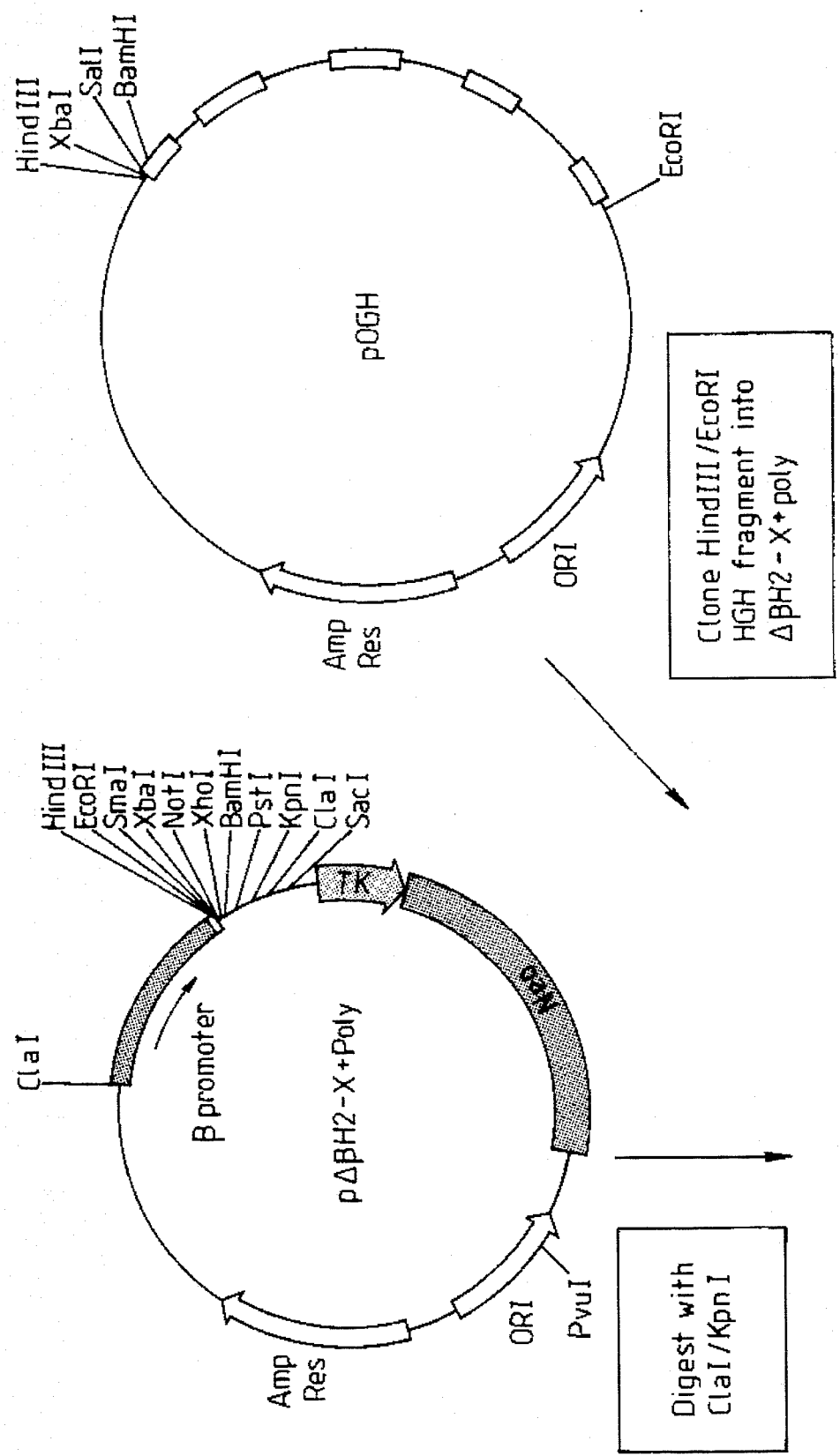
FIG. 7: Construction of HGH genomic expression vector.
Figure 7:
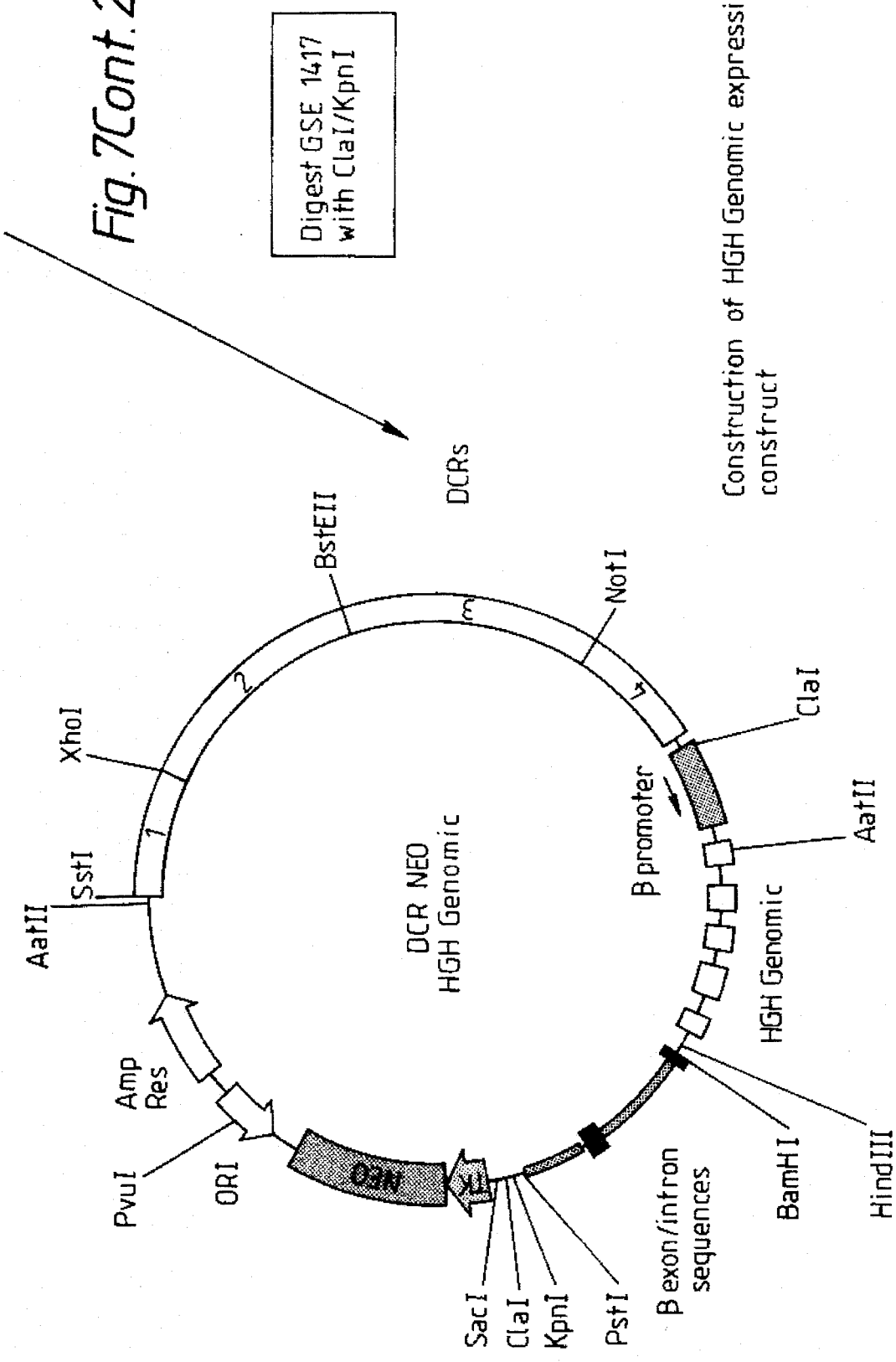

The HGH gene was prepared by restriction endonuclease digestion of plasmid pOGH which was obtained from the Nicholls Institute (see FIG. 7). An EcoRI to BamHI restriction fragment containing the native HGH genomic sequences from the natural mRNA start site to 620 bases after the translational stop codon was subcloned into the intermediate vector pΔBH2-X+Poly which lacks the β-globin intron/exon sequences (see FIG. 7) which normally provide the splice and polyadenylation functions for the chimaeric mRNA in our expression vectors. In this intermediate vector, the expression cassette consists of the human β-globin promoter coupled to the HGH genomic sequences (intron and exon sequences) and the HGH polyadenylation signals. This expression cassette was transferred into the final vector (GSE1417) as a ClaI-KpnI fragment as described for the HGH cDNA above. The final expression vector, pDCR/NEO/HGHgenomic, was introduced into MELC88 cells by electropotation and monoclonal transfectant lines and pooled populations were selected as described. As before, each transfected line was induced to differentiate and the secreted HGH was measured using a commercial RIA kit. The mRNA levels of the transfected gene were measured by Northern blotting with a HGH cDNA probe using the mouse β-major globin levels as an internal control.

Results - Example 2

As found with the expression of HGH from the HGH cDNA, the stable HGH gene transfectant cell lines, expressed and secreted HGH at high levels. Table 2 shows the levels of secreted HGH which were measured after a 4 day induction.

TABLE 2

Secretion of HGH from Transfected (gene) MELC88 Cells

| Cell Line | Monoclonal | [HGH] μg/ml |
|---|---|---|
| Electroporation | | |
| AP1 | NO | 12.0 |
| AP2 | NO | 7.0 |
| 1 | YES | 10.0 |
| 2 | YES | 24.0 |
| 3 | YES | 5.0 |
| 4 | YES | 3.0 |

Figure 8:
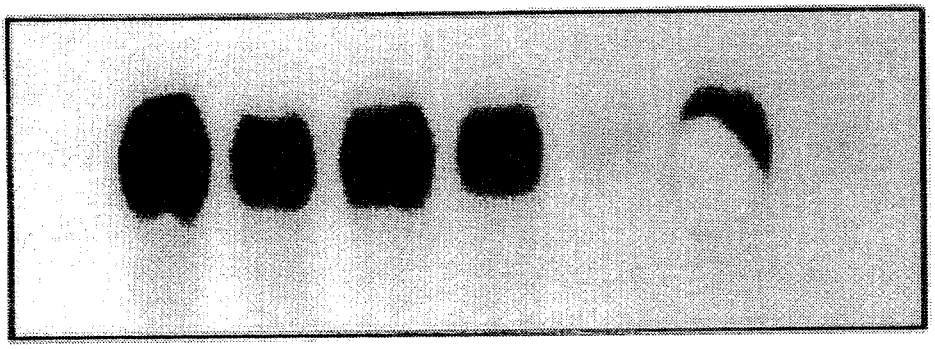
FIG. 8: Northern blot analysis of induced MELC88 lines transfected with the HGH genomic expression vector. In this Figure (i) indicates human growth hormone, and (ii) indicates mouse β-globin. lane A=AP1, lane B=AP2, lane C=clone 5, lane D=clone 1, lane E=clone 3, lane F=clone 2 and lane G=clone 4.
Figure 8:
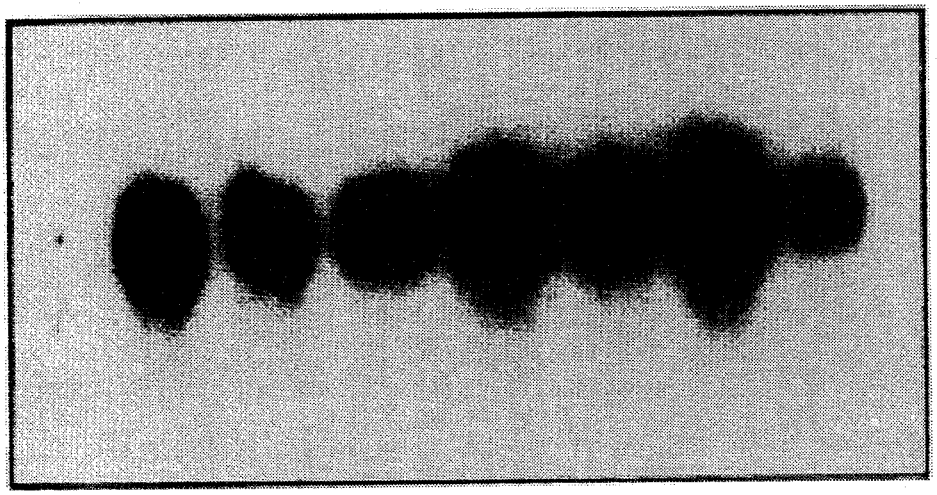
Figure 9:
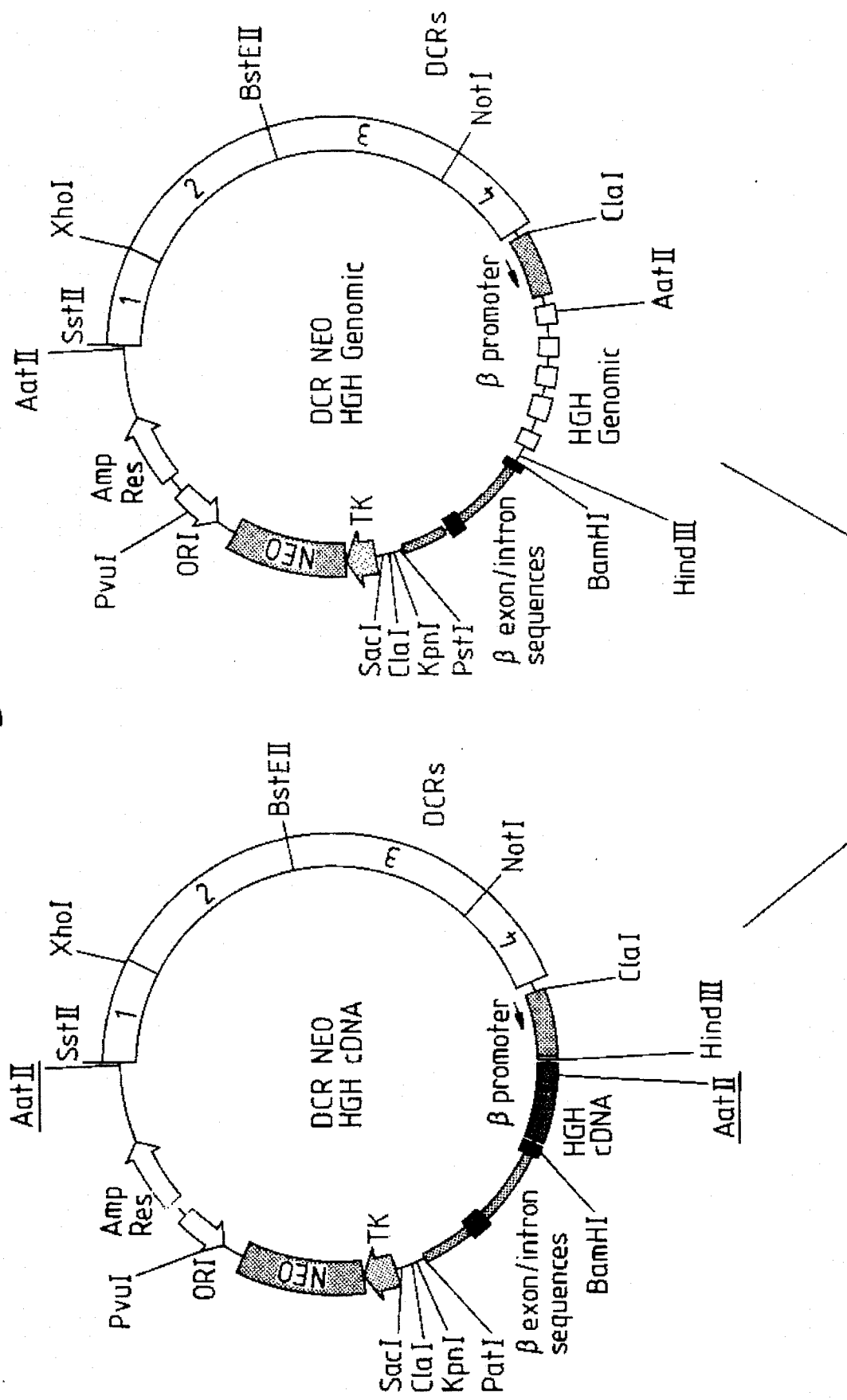
FIG. 9: Alteration of 5' end of HGH cDNA expression vector.
Figure 9:
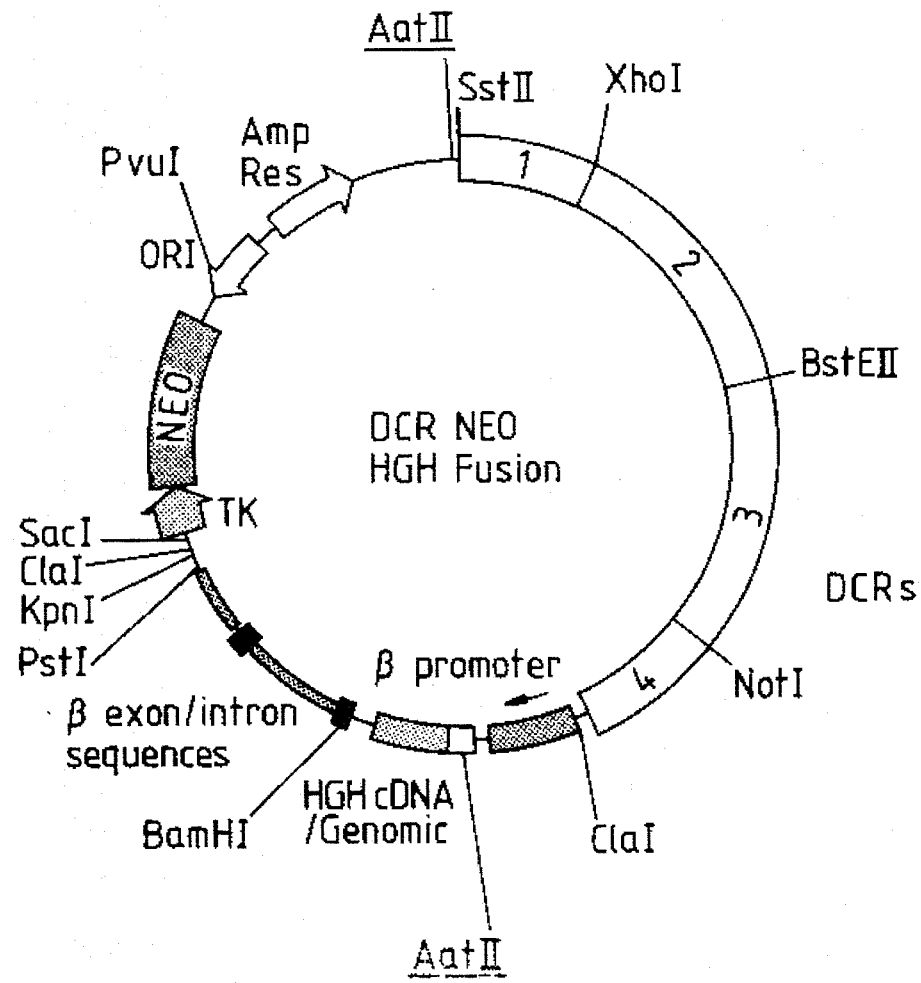

High level expression and secretion of HGH was observed in the stable transfected cell lines. The HGH mRNA level was measured by Northern blotting versus a HGH cDNA probe and again found to be roughly equivalent to the level of mouse β-major globin in the induced cells (see FIG. 8). Comparisons with the mouse β-major globin levels indicate that the levels of HGH mRNA are approximately equal from the cDNA expression vector (which uses the β-globin splice and polyadenylation sequences from pUNIVEC for processing) and the HGH genomic expression vector (which uses the natural HGH intron sequences and polyadenylation sequence for processing. The difference in secreted protein levels is probably accounted for by differences in the level of translation resulting from differences in the level of polyadenylation of the two mRNAs. Differences in the 5' ends (start) of the mRNAs do not contribute to the different translation levels observed since exchanging the 5' end of the HGH cDNA (still with human β-globin splice and polyadenylation sequences) with the mRNA start from the genomic HGH expression vector (see FIG. 9) did not affect levels of either mRNA or protein produced from the transfected cell lines.

Example 3 - Long Term Secretion of HGH

The level of secretion observed with the HGH cDNA or genomic DNA expression vectors was unexpected since the red blood cell is not normally a secretory cell. To obtain DCR driven expression, MEL cells must be induced to differentiate and become erythroid in character. This differentiation is a complex process which involves a number of physical changes to the cells and can result in enucleation of the cells and the selective degradation of mRNAs within the cells. The function of the erythroid cells in vivo, as carriers of oxygen (and dissolved carbon dioxide) over an approx 120 day lifespan is consistent with these changes. It is commonly accepted that the terminal differentiation also results in loss of the protein synthetic 'machinery' within the cell since this is essentially made redundant by the enucleation and mRNA degradation processes.

In the light of our high level secretion experiments we examined the production and secretion of HGH by transfected MEL C88 cells over an extended period of time. Cells transfected with the HGH cDNA expression vector were induced to differentiate as described before. After a period of approx 48 hours, the inducing medium (selective medium +2% DMSO) was replaced (with the same volume) and the original medium was assayed for HGH. The medium was subsequently replaced every 24–36 hours (to avoid cell death due to nutrient/factor depletion) for a period of approx 80 days.

Results - Example 3

Figure 10:
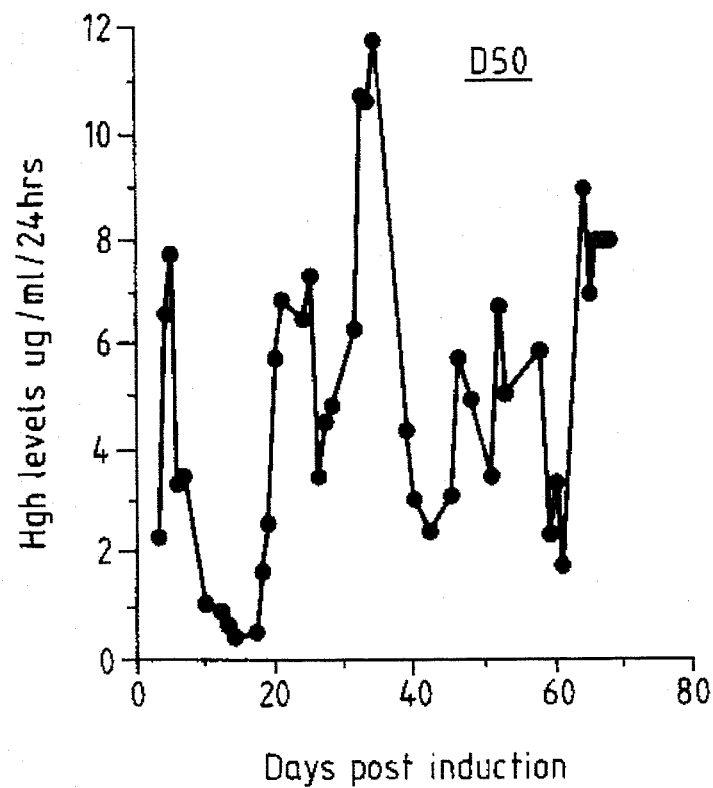
FIG. 10: Long term secretion of two HGH cDNA clones in MelC88 cells.
Figure 10:
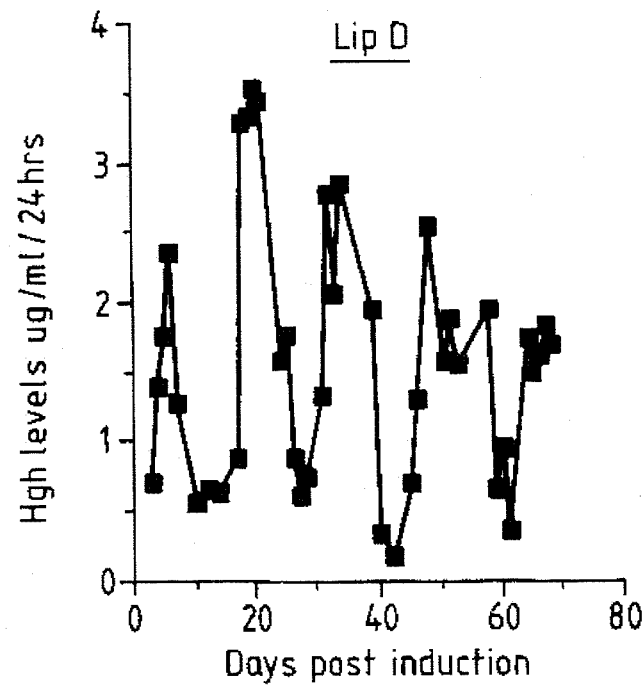

FIG. 10 shows the levels of HGH produced and secreted over this extended induction period. It is not clear if the fluctuation in HGH levels seen represent changes in the level of secretion from a stable population of cells or if some subpopulation of cells fail to induce at the start of the experiment and subsequently 'mature' and induce at later times. What is clear from the experiment is that the induced MELC88 transfectant cell lines can continue to produce secreted HGH for at least 80 days after the start of induction. Again, this was unexpected due to the cellular changes which accompany terminal erythroid differentiation.

The duration of secretion observed has implications for use of the transfected cell lines in a prolonged production process. In addition, the long term secretion suggested that the system may be useful to produce secretory proteins in the bloodstream of mammals either as a production process or as part of a gene-therapy protocol.

Example 4 - Inhibition of secretion

The report that the fungal metabolite, brefeldin-A, inhibits glycophorin movement to the cell surface in MEL cells by specifically blocking flux through the Golgi apparatus (Ulmer & Palade PNAS 86 6992–6996 (1989)) allows investigation of the ability of erythroid cells to secrete heterologous proteins.

A clone of MELC88 expressing HGH was induced with 1.5% DMSO for 3 days and then 1 µg/ml of brefeldin-A in ethanol added. Control cultures contained 0.1% ethanol. After incubation at 37° C. for 2 hours the cultures were washed twice with fresh medium and brefeldin-A (1 µg/ml) or ethanol (0.1%) added to treated and control cultures respectively. Samples of supernatant and cells were then taken for analysis.

Results - Example 4

Growth hormone levels in the culture supernatants and in sonicated cell extracts were measured using the sandwich immunoradiometric assay described earlier. Samples were analysed at 1, 2 and 4 hours after the medium was changed.

TABLE 3

HGH Secretion from Brefeldin-A Treated Cells

| TIME (hours) | CONTROL | | BREFELDIN A | |
| --- | --- | --- | --- | --- |
| | supernatant ng/ml | cell lysate ng/ml of cells | supernatant ng/ml | cell lysate ng/ml of cells |
| 1 | 162 | 52.6 | 47.1 | 183 |
| 2 | 209 | 96.0 | 44.0 | 515 |
| 4 | 331 | 71.0 | 54.0 | 777 |

As can be seen, control cultures accumulated HGH in the supernatants in a time dependant manner while there was no increase in cellular levels. Conversely there was no increase in supernatant HGH levels but an increase in cellular HGH levels in brefeldin A treated cultures. This data clearly shows that the appearance of HGH in the supernatant is due to the secretion of the protein through the Golgi apparatus.

Example 5 - Secretion of Other Recombinant Proteins - Human PLA$_2$ cDNA

The secretion experiments described with HGH indicated that the system we describe is capable of expressing and secreting large quantities of recombinant protein. The nature of the system, with very limited expression until the cells are induced to terminally differentiate, is versatile and applicable to a wide variety of protein types. Even proteins which are toxic or destructive to cells could be expressed in this system. We tested expression of one such protein, the human synovial phospholipase A$_2$, in the MEL cell secretion system.

Phospholipase A$_2$ is an enzyme involved in the metabolism of membrane phospholipids. The enzyme specifically cleaves one of the fatty acid chains of phosphatidyl choline or phosphatidyl ethanolamine within cell membranes to release arachidonic acid (which is part of the inflammatory pathway). The remaining lyso-phospholipids have detergent properties in the cell membranes. Expression of phospholipase A$_2$ in animal cells is probably limited by the destructive effects of the PLA$_2$ on the producing cells. To date, the highest level of expression reported is >200 ng/ml in amplified CHO cells (Kramer et al., J. Biol. Chem. 264, 5768–5775, 1989).

Figure 11:
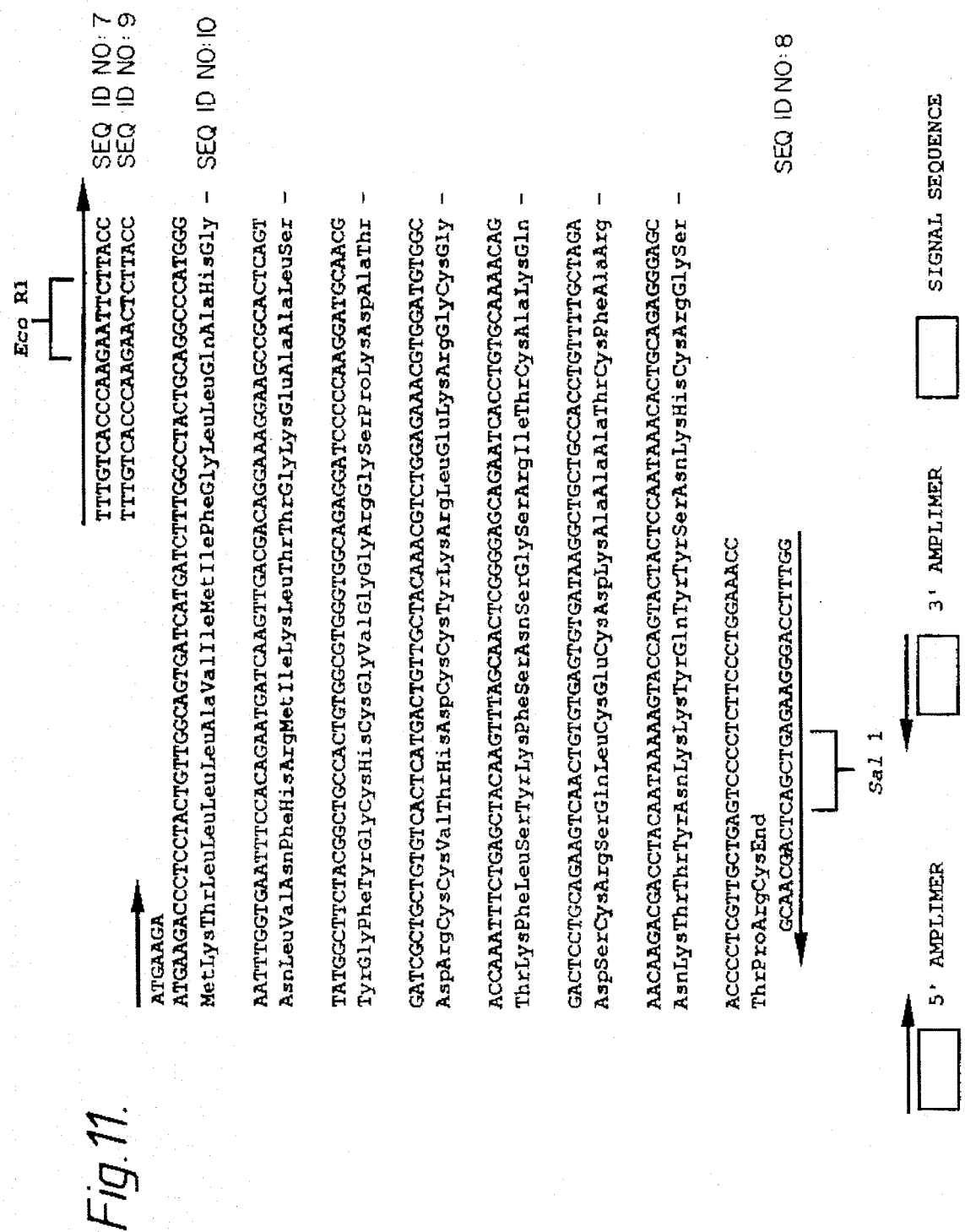
FIG. 11: cloning of PLA$_2$ cDNA (see SEQ ID NO:7 to SEQ ID NO:10).
Figure 11:
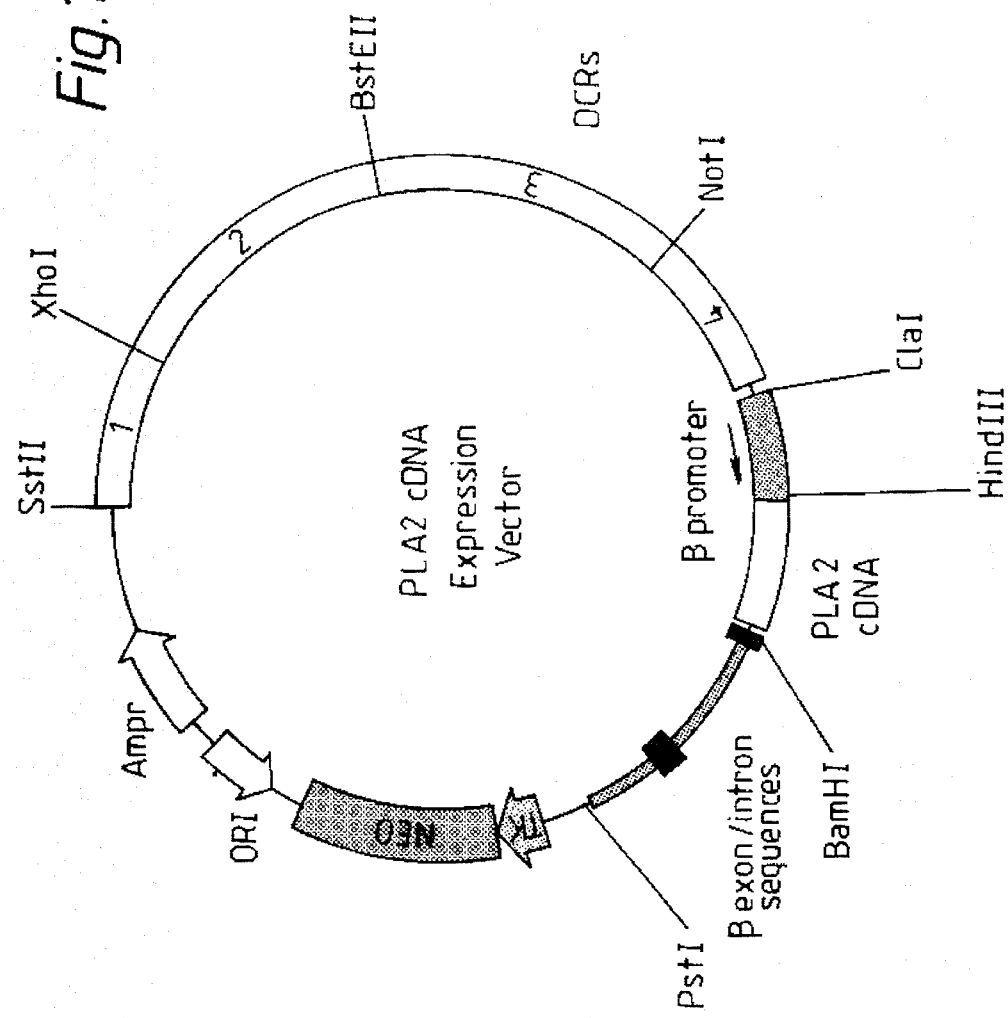
Figure 12:
FIG. 12: Cloning of the PLA2 gene into the expression vector.
Figure 12:
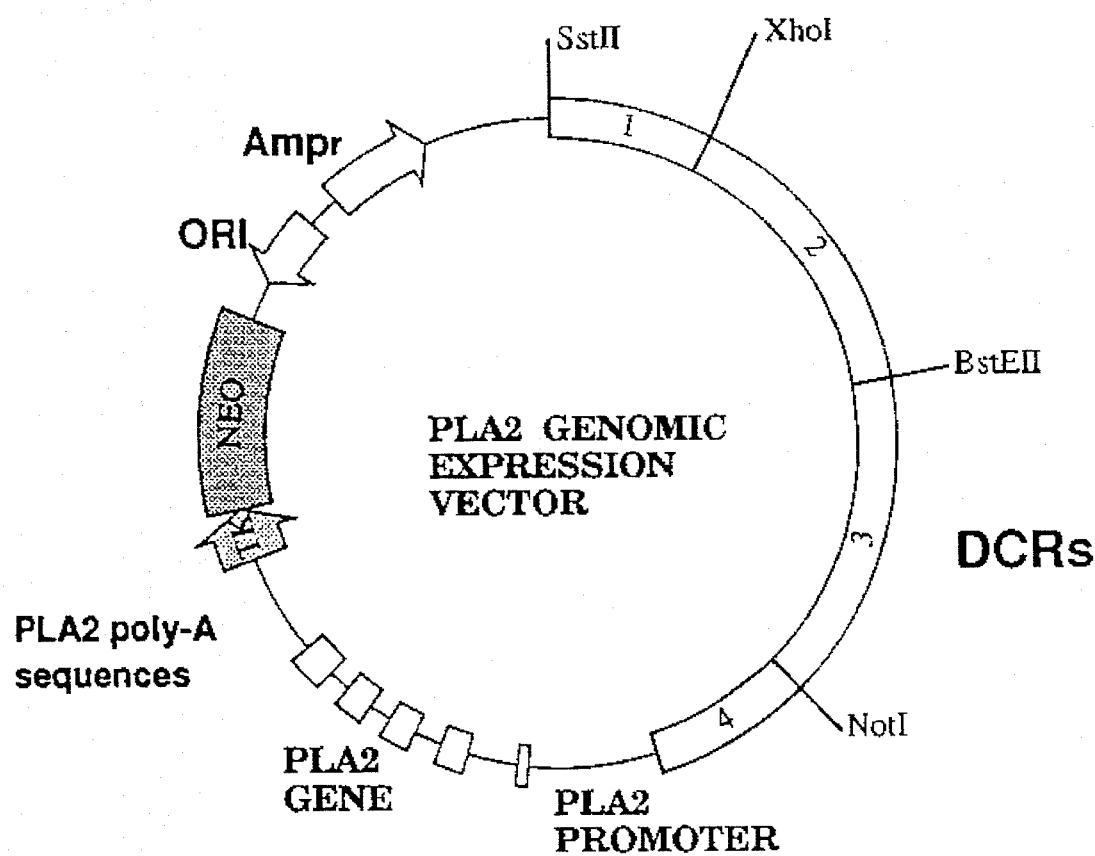

To express the human PLA$_2$ in our MEL cell expression system we first cloned the PLA$_2$ from a human lung cDNA library using the polymerase chain reaction (PCR) technique. The PCR amplimers used and the PLA$_2$ cDNA sequence are shown in FIG. 11. The cDNA was then subcloned into the intermediate plasmid pUNIVEC as an EcoRI to SalI fragment (into the EcoRI and XhoI sites of pUNIVEC). The expression cassette was then transferred as a ClaI to KpnI fragment into pGSE1417 as described above.

Transfectant cell lines were generated as described above and following induction, the supernatants were assayed for PLA$_2$ activity.

Results - Example 5

Induced, transfected MELC88 cultures were assayed for phospholipase activity using two methods. The first (see Pepinski et al., J. Biol. Chem. 261, 4239–4246, 1986) uses E. coli membranes labelled in vivo with [$^3$H]oleic acid as substrate and the second (see Seilhamer et al., J. Biol. Chem. 264, 5335–5338, 1989) uses phosphatidyl choline or phosphatidyl ethanolamine as substrates for the PLA$_2$. The supernatants from the transfected MEL cell clones were active in both assays and (since the second assay gave more reproducible results) gave expression levels of approx 200 ng/ml. It can be seen that, without need for lengthy optimisation studies, the transfected MELC88 cells secreted as much active recombinant human phospholipase A$_2$ as the best published figure to date (Kramer et al., J. Biol. Chem. 264, 5768–5775, 1989) using amplified expression in CHO cells but in a considerably shorter time.

Example 6 - Expression of PLA$_2$ using native PLA$_2$ genomic sequences

The PLA$_2$ genomic sequences were isolated as a 6.2 kb HindIII fragment from a human placental genomic DNA library (Clontech Ref HL1067J) using the cloned PLA$_2$ cDNA as a probe. This clone was characterised by restriction enzyme digestion and shown to contain a the PLA$_2$ genomic sequences. The entire fragment (containing the PLA$_2$ coding and intervening sequence DNA, polyadenylation site and approx 1.5 kb of putative promoter sequence upstream [5'] of the first exon was cloned into the vector pGSE1417. In this plasmid, expression of the PLA$_2$ sequences is controlled by the native PLA$_2$ promoter. The plasmid was linearised by restriction digestion with PvuI and introduced into MELC88 cells as described earlier. Pooled populations and monoclonal lines were selected and induced and secreted PLA$_2$ levels were measured as before.

Results - Example 6

The expression of PLA$_2$ from the PLA$_2$ promoter (measured by protein levels (see Table 4A below) or RNA levels (see FIG. 13)) was significantly higher than the expression levels seen with the PLA$_2$ cDNA using the human β-globin promoter. The highest level of secretion was 2.5 μg/ml which is an order of magnitude greater than the level seen using conventional CHO/DHFR systems. The difference between the expression levels seen with the PLA$_2$ cDNA and genomic sequences is probably a consequence of the higher stability of the mRNA made from the genomic template since substituting the human β-globin promoter for the human PLA$_2$ promoter in the PLA$_2$ gene construct does not effect the levels of secreted PLA$_2$ seen. The results of expression of the PLA2 genomic sequences using the β-globin promoter are shown in Table 4B.

TABLE 4

PLA$_2$ Assays

| Sample | Monoclonal | μg/ml |
|---|---|---|
| A. PLA2 gene with PLA2 promoter | | |
| PP1 | NO | 1.5 |
| PP2 | NO | 1.5 |
| 1 | YES | 2.3 |
| 2 | YES | 2.5 |
| 3 | YES | 0.9 |
| 4 | YES | 1.6 |
| B. PLA2 gene with the human β-globin promoter | | |
| ΔPP | NO | 0.34 |
| Δ1 | YES | 1.72 |
| Δ3 | YES | 1.10 |
| Δ4 | YES | 0.38 |
| Δ6 | YES | 1.66 |

Example 7 - Expression of HGH in MEL11A21 Cells

We have demonstrated that MELC88 cells are capable of efficient secretion of recombinant proteins. In order to make protein purification and recovery of the recombinant protein easier, we have also examined the expression in other murine erythroleukaemia cell lines. The MEL cell line 11A21 is maintained in non-selective media with 1% foetal calf serum as described. The reduction in serum content from 10% to 1% greatly reduces the contaminating proteins in the final preparation and facilitates protein purification. We have expressed HGH in 11A21 cells. The expression vectors pDCR/NEO/HGHcDNA and pDCR/NEO/HGHgenomic are as described earlier. Transfections and selection were as described for MELC88 except that 1% serum was used throughout. The induction was carried out as described except that inducing medium for 11A21 transfectant cells has 1% foetal calf serum +αMEM.

Results - Example 7

Table 5 shows the secreted HGH levels seen upon induction of 11A21 transfectant cell lines. When corrected for cell numbers, these cells secrete as well as the C88 transfectants indicating that the vectors can drive expression and, if appropriate, secretion in a range of MEL cell types.

TABLE 5

HGH Expression from 11A21 Transfectants

| Cell Line | Monoclonal | [HGH] μg/ml |
|---|---|---|
| PP1 | No | 1.2 |
| PP2 | No | 1.0 |
| 1 | Yes | 2.0 |
| 2 | Yes | 0.9 |
| 3 | Yes | 0.6 |
| 4 | Yes | 1.2 |

Example 7b - expression of hGH cDNA under control of PLA2 promoter.

Expression of human growth hormone cDNA under the control of the PLA$_2$ promoter was achieved as follows. The PLA$_2$ promoter was isolated from human DNA using the PCR technique as described above (Example 5). The PLA2 promoter was obtained as a 200 bp fragment using the following PCR amplimers (SEQ ID NO: 3 and SEQ ID No:4)

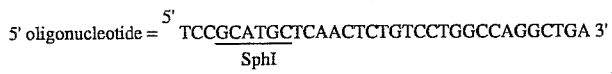

5' oligonucleotide = 5' TCCGCATGCTCAACTCTGTCCTGGCCAGGCTGA 3'
SphI

3' oligonucleotide = 5' CAGAAGCTTCCAGAGTTGTATCCCCAGGCCGTC 3'
HindIII

The PCR product was used to replace the human β-globin promoter in pEC3 (SphI-Hind III) to produce a new vector pEC4, into which the human growth hormone cDNA was cloned using HindIII-Bam HI sites. The final expression vector was formed by transferring the ClaI-Asp718 cassette of pEC4 into pGSE1417 to give phGH.4GSE.

Supernatants from cells induced for four days were tested for growth hormone. Samples: hGH508, a positive control of hGH cDNA downstream of the β-globin promoter; PP1 and PP2, pooled populations; 1–4, individual clones.

| Sample | Induction I (μg/ml) | Induction II (μg/ml) | Induction III (μg/ml) |
|---|---|---|---|
| hGH508 | 17.3 | 15.0 | 18.4 |
| PP1 | 7.3 | 9.0 | 9.6 |

| Sample | Induction I (μg/ml) | Induction II (μg/ml) | Induction III (μg/ml) |
|---|---|---|---|
| PP2 | 9.9 | 11.7 | 14.9 |
| 1 | 6.5 | 3.2 | 8.9 |
| 2 | 6.3 | 7.0 | 9.2 |
| 3 | 1.9 | 2.4 | 3.1 |
| 4 | 12.7 | — | 25.6 |

Example 8 - Stability of Secretion Level After Long Term Culture

A major drawback of amplification based expression systems is the stability of the amplified sequences. Until recently it was generally agreed that amplified sequences integrated into the genome would be stable without pressure. However, data from industrial research groups indicates that such amplifications can be unstable even in the presence of selection pressure (eg Weidle U H et al Gene 66 193–203 (1988)). These problems should not be encountered with the DCR expression system since large copy numbers are not needed for high level expression.

To test this hypothesis, five clones were derived from the high producing cell line $D_{50}$ by multiple limiting dilution cloning. The clones were then passaged over 40 generations with and without selection pressure G418. Due to possilbe variations in the inducibility of the clones the productivity was ascertained compared with the uninduced clones of cells. No alteration in productivity was seen over extended growth in the absence of selection, suggesting that the expression construct was stable in the cells.

Example 9 - Stability of RNA Produced from The Expression Vectors

Figure 13A:
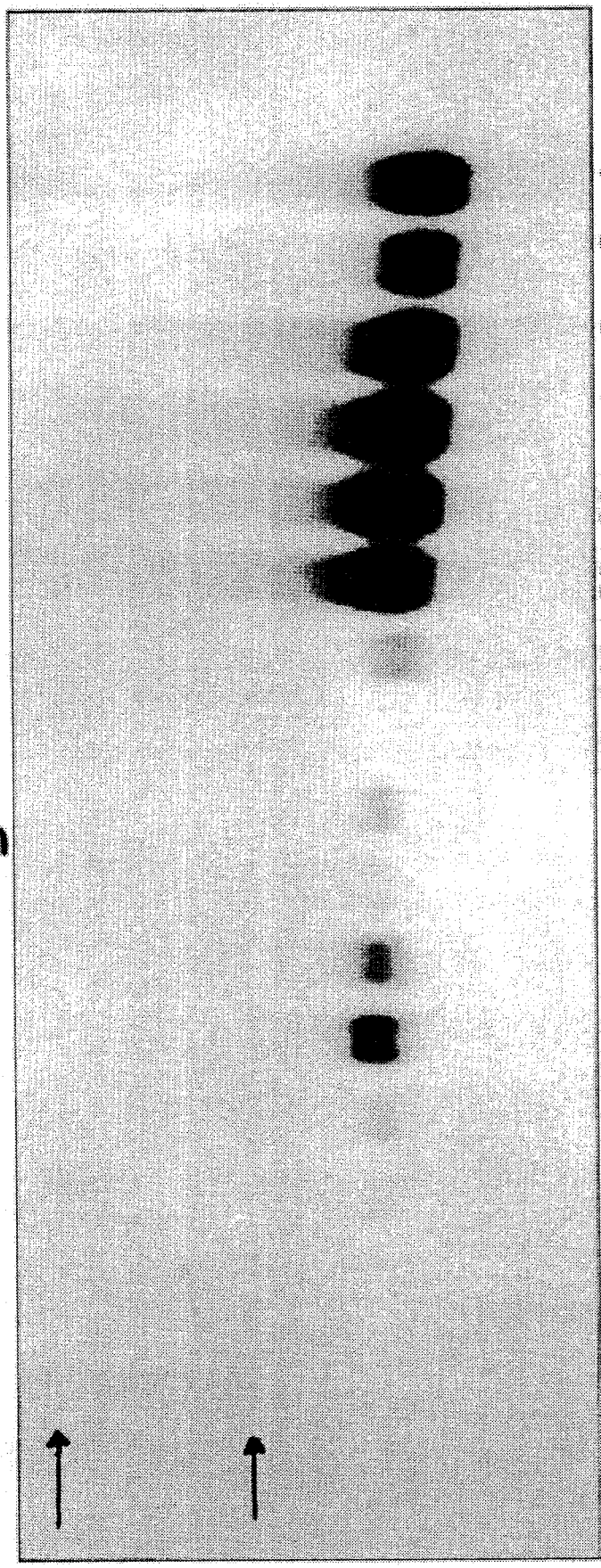
FIG. 13(a)=probed with PLA2, (b)=probed with mouse β-globin, and (c)=probed with GAPDH.
Figure 13B:
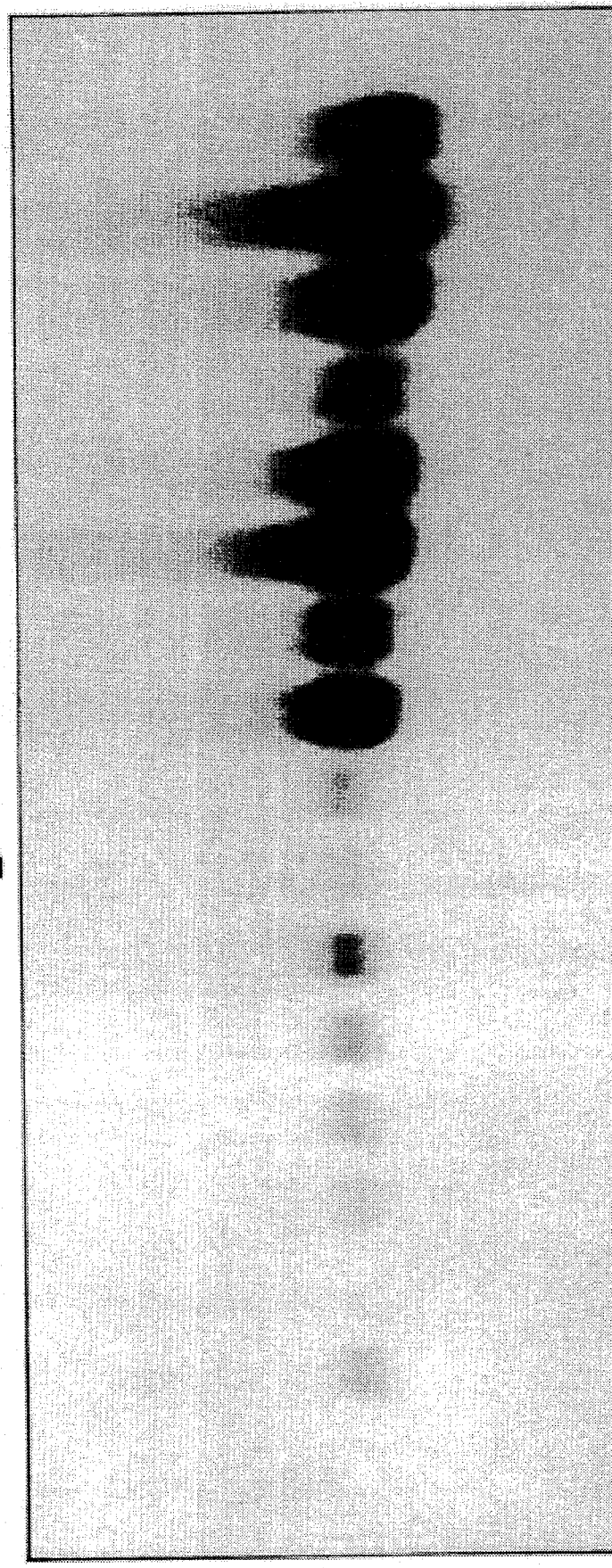
FIG. 13: Northern blot of PLA2 expression from the PLA2 genomic sequences. In this Figure NI=non-induced, I=induced, MEL= MelC88, 50C-1=PLA2 cDNA clone, PP1, PP2=pooled populations of PLA2 transfected MelC88 cells, and 1,2,3 and 4=individual clones of PLA2 transfected MelC88 cells.
Figure 13C:
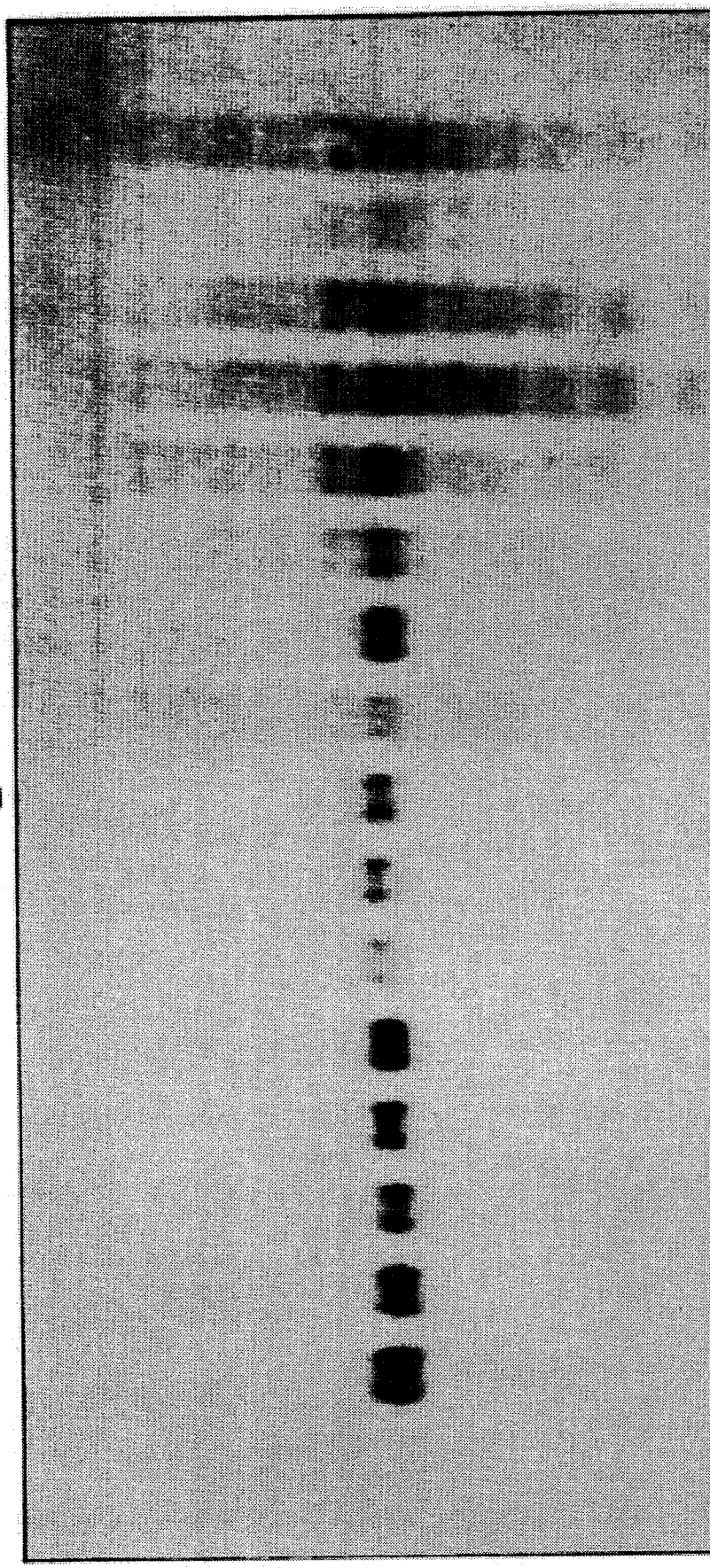
Figure 14A:
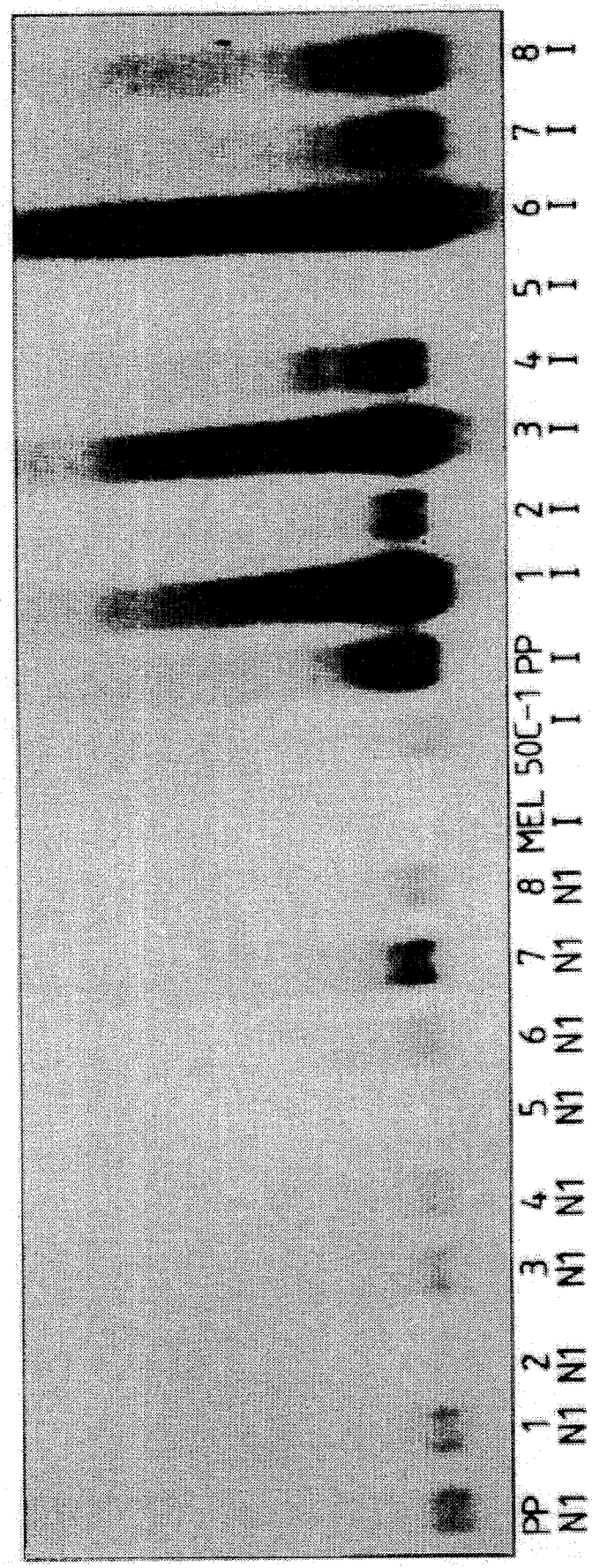
FIG. 14: Northern blot of PLA2 expression from the "β-globin promoter/PLA2 coding"0 construct. In this FIG. I=induced, NI=non-induced, MEL=MelC88, PP=pooled population, 1,2,3,4,5,6,7 and 8 are individual clones, 50C-1=PLA2 cDNA clone.
Figure 14B:
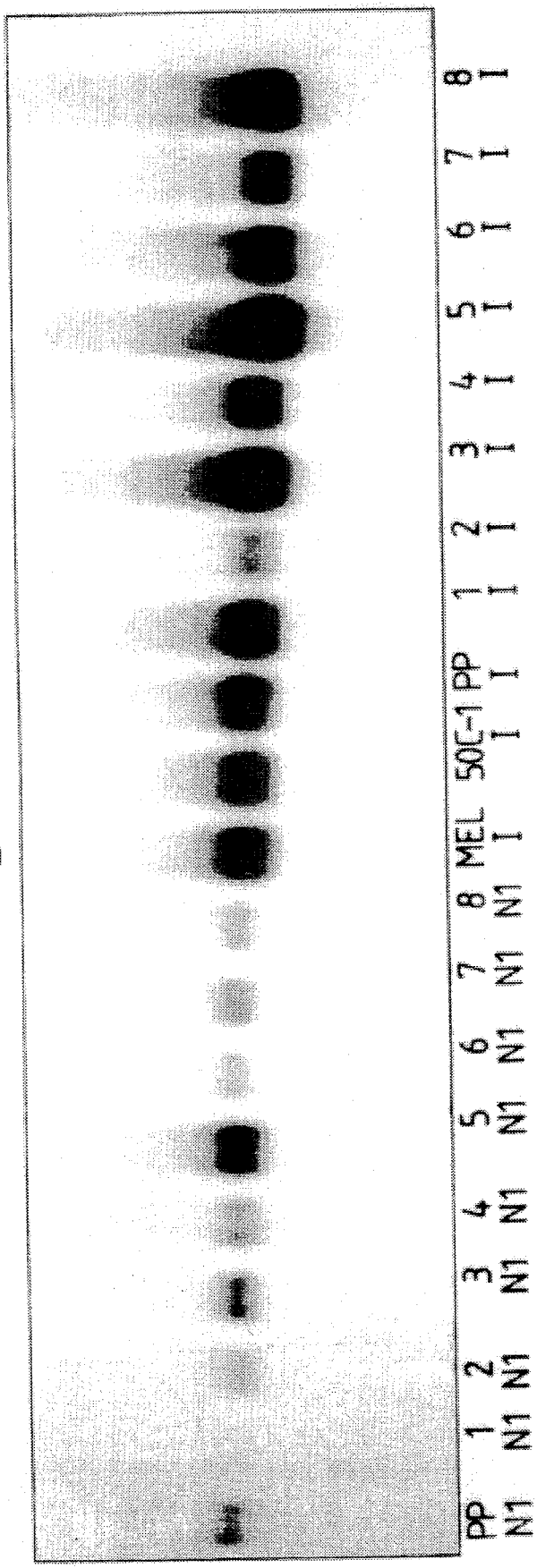
Figure 14C:
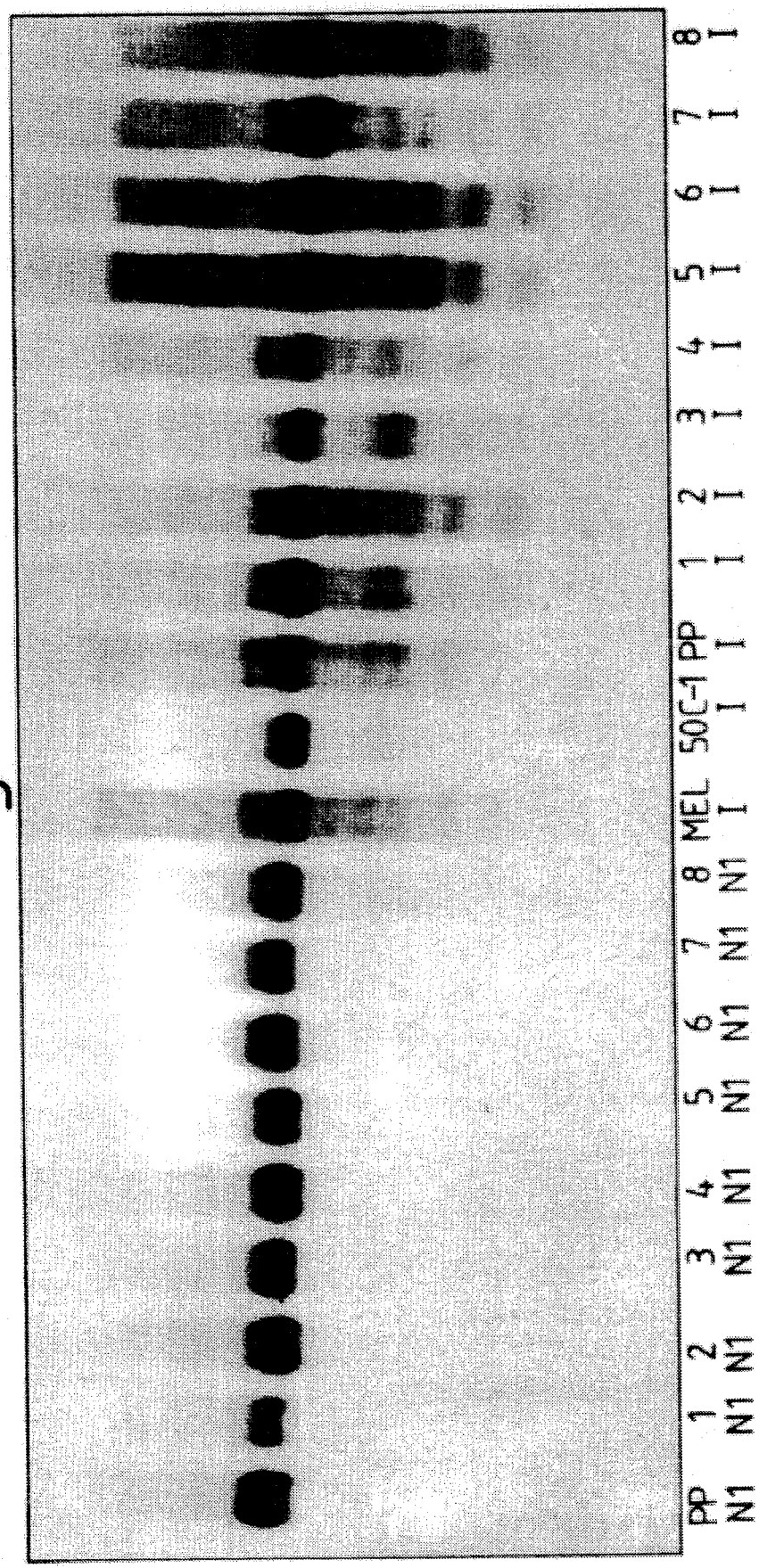

As described earlier (see Example 3) erythroid differentiation is a complex process which involves many steps and results in the selective degradation of many mRNAs within the cells. In order to maintain high level expression of heterologous cDNAs or genes, the heterologous mRNA must be stable in the induced red cells. In order to maintain the mRNA integrity in induced cells, we have used parts of the 3' ends of the β-globin mRNA in our cDNA expression constructs. This stabilising effect can also be provided by portions of the 3' ends of other genes which produce stable messages in induced red cells (eg HGH or PLA2) but can not be provided by genes which produce highly unstable mRNAs in the induced cells (eg mouse H2K). FIGS. 13 and 14 illustrate this point and compare heterologous PLA2 messages (from a variety of constructs with the endogenous glyceraldehyde 3 phosphate dehydrogenase (GAPDH) mRNA. The PLA2 mRNAs remain stable in induced cells but the GAPDH mRNA is degraded in all the induced samples.

Example 10 - Expression of human Growth hormone in $pEC_3$ $pEC_3$ is identical to $pEC_2$ other than it contains a longer region of β-globin 3' flanking DNA than $pEC_2$ (i.e. up to the natural Xba I site at base 4845) in the β-globin gene, and different polylinker cloning sites between the Hind III and BamH I sites of the $pEC_1$ polylinker.; Hind III, EcoR I, XhoI, Bal II, Sal I, Not I and BamH I. The Hgh cDNA was subcloned into $pEC_3$ (HindIII/Bam HI) then the ClaI/Asp718 fragment from this clone was subcloned into pGSE1417. Transfection, induction, RNA analysis and hGH analysis were carried out as before. The results are illustrated in FIG. 22.

6 clones and 2 populations each for $pEC_2m$/hGH - $pEC_3$/hGH expressing cells were induced and assayed for hGH expression. The results show that the level of hGH seen with $EC_3$ is greater than with $EC_2$. Thus the construct with longer 3' end gives high levels of hGH. This could be (although we do not wish to be bound by this theory) due to the longer 3' end improving translational efficenty.

Example 11 - Major Basic Protein (MBP)

We have expressed the MBP cDNA (see Mcgrogan et al, J. Exp. Med., 1988, 168, 2295–2308; and Barker et al, Gene, 1990, 86, 285–289) using the expression vector $pEC_3$. The MBP cDNA was subcloned as a BamHI fragment into $pEC_3$ then the ClaI/Asp 718 fragment from this construct was subcloned into pGSE1417.

Transfections, induction and RNA analysis were carried out as in previous examples. The results are illustrated in FIG. 15.

Supernatant from induced clones 2a and 2e were used in an E-coli killing assay (see FIG. 16) using a suitable E.coli killing assay such as one based on the method of Gleich et al, J. Exp. Med., 1974, 140, 313–332. In the present case the procedure used was briefly as follows.

An overnight culture of E. coli (for example, E. coli DHSα) was centrifuged at 10 Kpm for 1 minute then resuspended in 1 ml of distilled water. 10 μl of this culture was mixed with 90 μl of Mel cell supernatants and incubated at room temperature for 1 hour. Samples were then serially diluted and then spot plated on to L-Broth plates.

Example 12 - TNFα Receptor

The soluble extracellular domain of the TNFα Receptor (A) (see published European Patent Application No. 422,339) was expressed in Mel C88 cells by subcloning the cDNA and a DNA fragment encoding a "CMYC tag" (a part of the CMYC cDNA which encodes a strech of amino acids to which a monoclonal antibody binds) into $pEC_3$ (Bam HI) then into pGSE1417.

Transfections, Induction and RNA analysis were carried out as before. The results are illustrated in FIG. 17.

10 clones were induced and TNFα Receptor levels measured using binding to an anticmyc-antibody (see FIG. 18) and their ability to bind TNFα was measured using an anti TNF antibody (see FIG. 18).

Example 13

$NK_2$ receptor cDNA (Graham et al, Biochemical & Biophysical research Communications, 1991, 177 No. 1, 8–16) was subcloned into $PEC_3$ and then the ClaI/Asp718 fragment from this construct was subcloned into GSE1417 to give plasmid pGSE 1417/hNK-2R (10 kb). After growth in E. coli and linearisation the resulting construct was used to transfect MEL C88 cells. Expressing clones are selected with G418 and induced with DMSO.

MEL cell transfection

MEL C88 cells were electroporated with PvuI linearised GSE1417/hNK-2R. After selection with G418 for 4 days, 6 single colonies were picked and the remainder pooled to give 2 clone pools. These were grown 3–4 splits to ensure G418 resistance. Following induction with 2% DMSO the cells were grown for 4 days both in the presence and absence of 50 μM of an $NK_2$ receptor antagonist before harvesting. Cell pellets were subsequently used for binding assays, RNA preparation for Northern blots, and SDS/PAGE analysis.

Northern blots

20 μg of total RNA isolated from each of the clones was electrophoresed, blotted and probed with human NK-2 receptor cDNA. The blot was and re-probed with a 200 bp fragment from intron 2 of the murine β-globin gene (murine specific). FIG. 20 shows a 4 hr exposure of a Northern blot of RNA prepared from MEL cell transfectants probed with hNK-2R. Notably the hNK-2R mRNA appears as 2 distinct species—1.6 kb and 3 kb. These bands are absent in RNA from untransfected induced and co-transfected uninduced MEL C88 controls. Clone 2 also does not show detectable levels of hNK-2R transcription and this agrees with very low levels of detectable NKA binding. The occurrence of 2 NK-2R hydridising bands is attributable to the presence of both spliced and unspliced message. FIG. 19 show the same blot exposed for 3 hr after probing with β-globin. This shows that the steady state mRNA level of hNK-2R is equivalent to that of the mouse globin gene.

NKA Binding assay

Partially purified membranes from MEL cell pellets were used in an $^{125}$I Neuro-kinine A (NKA) binding (NKA at 100 nM) assay (Table 3).

TABLE 3

|   | − antagonist $I^{125}$ NKA binding (fmol/mg) | + antagonist $I^{125}$ NKA binding (fmol/mg) |
|---|---|---|
| 1 | 329.69 | 990.87 |
| 2 | 1.49 | 252.87 |

TABLE 3-continued

|   | − antagonist $I^{125}$ NKA binding (fmol/mg) | + antagonist $I^{125}$ NKA binding (fmol/mg) |
|---|---|---|
| 3 | 201.85 | 311.20 |
| 4 | 154.11 | 304.41 |
| 5 | 170.90 | 265.00 |
| 6 | 106.85 | 137.90 |
| 104 | 91.53 | 137.54 |
| 105 | 118.67 | 8.46 |
| MelC88 induced | 11.20 | 18.11 |
| MelC88 uninduced | 0 | — |

Results indicate that clone #1 expresses hNK-2R at the highest level both in the presence and absence of antagonist. Expression in the presence of antagonist appears to be 3-fold higher in this cell-line. The presence of antagonist appears to have variable effects on the detectable binding activities. Controls show a low background of NKA binding in thse assays.

Example 14 - Human serum albumen

Human serum albumen (HSA) cDNA (see, for example Sargent et al, Proc. Nat. Acad. Sci., USA, 1981, 78, 243–246) was subcloned into pEC3 then the ClaI/Asp 718 fragment transferred into pGSE 1417.

Transfections, induction and RNA analysis were as before, with the result that expression of HSA in mel cells was obtained.

We claim:

1. An expression system which comprises murine erythroleukemia cells transformed with a vector which comprises (i) the human beta-globin promoter, (ii) a genomic DNA sequence which codes for a polypeptide heterologous to said murine erythroleukemia cells and (iii) a dominant control region, and wherein after induction of differentiation of said murine erythroleukemia cells, said polypeptide is secreted by said murine erythroleukemia cells.

2. The expression system of claim 1 wherein the dominant control region comprises a micro locus which comprises a 6.5 kb fragment obtained by ligating the fragments:

2.1 kb XbaI - XbaI;

1.9 kb HindIII - HindIII;

1.5 kb KpnI - BgIII; and 1.1 kb partial SacI; from the β-globin gene.

3. A method of preparing a polypeptide, said method comprising cultivating the expression system according to claim 1.

4. An expression system which comprises murine erythroleukemia cells transformed with a vector which comprises (i) the human beta-globin promoter, (ii) the second exon/intron, 3rd exon and polyadenylation sequence, all of the human beta-globin gene, (iii) a cDNA sequence which codes for a polypeptide and (iv) a dominant control region, and wherein after induction of differentiation of said murine erythroleukemia cells, said polypeptide is secreted by said murine erythroleukemia cells.

5. The expression system of claim 4 wherein the dominant control region comprises a micro locus which comprises a 6.5 kb fragment obtained by ligating the fragments:

2.1 kb XbaI - XbaI;

1.9 kb HindIII - HindIII;

1.5 kb KpnI - BgIII ; and 1.1 kb partial SacI; from the β-globin gene.

6. A method of preparing a polypeptide, said method comprising cultivating the expression system according to claim 4.

* * * * *

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 65 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:1:

```
AGCTTGAATT CCCCGGGTCT AGAGCGGCCG CCTCGAGGGA TCCCTGCAGG TACCATCGAT      60

GAGCT                                                                 65
```

( 2 ) INFORMATION FOR SEQ ID NO:2:

( i ) SEQUENCE CHARACTERISTICS:
        ( A ) LENGTH: 57 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:2:

```
CATCGATGGT ACCTGCAGGG ATCCCTCGAG GCGGCCGCTC TAGACCCGGG GAATTCA        57
```

( 2 ) INFORMATION FOR SEQ ID NO:3:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

TCCGCATGCT CAACTCTGTC CTGGCCAGGC TGA        33

( 2 ) INFORMATION FOR SEQ ID NO:4:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

CAGAAGCTTC CAGAGTTGTA TCCCCAGGCC GTC        33

( 2 ) INFORMATION FOR SEQ ID NO:5:

( i ) SEQUENCE CHARACTERISTICS:
        ( A ) LENGTH: 33 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:5:

AGCTTGCCAC CATGGCTACA GGCTCCCGGA CGT        33

( 2 ) INFORMATION FOR SEQ ID NO:6:

( i ) SEQUENCE CHARACTERISTICS:
        ( A ) LENGTH: 24 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:6:

CCGGGAGCCT GTAGCCATGG TGGC        24

( 2 ) INFORMATION FOR SEQ ID NO:7:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

TTTGTCACCC AAGAATTCTT ACCATGAAGA        30

( 2 ) INFORMATION FOR SEQ ID NO:8:

( i ) SEQUENCE CHARACTERISTICS:
        ( A ) LENGTH: 30 base pairs
        ( B ) TYPE: nucleic acid (C) STRANDEDNESS: single
(D) TOPOLOGY: linear (ii) MOLECULE TYPE: cDNA (xi) SEQUENCE DESCRIPTION: SEQ ID NO:8:

GGTTTCCAGG GAAGAGTCGA CTCAGCAACG                         30

(2) INFORMATION FOR SEQ ID NO:9:

(i) SEQUENCE CHARACTERISTICS:
    (A) LENGTH: 479 base pairs
    (B) TYPE: nucleic acid
    (C) STRANDEDNESS: single
    (D) TOPOLOGY: linear (ii) MOLECULE TYPE: cDNA (ix) FEATURE:
    (A) NAME/KEY: CDS
    (B) LOCATION: 24..455

(xi) SEQUENCE DESCRIPTION: SEQ ID NO:9:

```
TTTGTCACCC AAGAACTCTT ACC ATG AAG ACC CTC CTA CTG TTG GCA GTG       50
                         Met Lys Thr Leu Leu Leu Leu Ala Val
                          1               5

ATC ATG ATC TTT GGC CTA CTG CAG GCC CAT GGG AAT TTG GTG AAT TTC     98
Ile Met Ile Phe Gly Leu Leu Gln Ala His Gly Asn Leu Val Asn Phe
 10              15                  20                      25

CAC AGA ATG ATC AAG TTG ACG ACA GGA AAG GAA GCC GCA CTC AGT TAT    146
His Arg Met Ile Lys Leu Thr Thr Gly Lys Glu Ala Ala Leu Ser Tyr
             30                  35                      40

GGC TTC TAC GGC TGC CAC TGT GGC GTG GGT GGC AGA GGA TCC CCC AAG    194
Gly Phe Tyr Gly Cys His Cys Gly Val Gly Gly Arg Gly Ser Pro Lys
             45              50                  55

GAT GCA ACG GAT CGC TGC TGT GTC ACT CAT GAC TGT TGC TAC AAA CGT    242
Asp Ala Thr Asp Arg Cys Cys Val Thr His Asp Cys Cys Tyr Lys Arg
             60              65                  70

CTG GAG AAA CGT GGA TGT GGC ACC AAA TTT CTG AGC TAC AAG TTT AGC    290
Leu Glu Lys Arg Gly Cys Gly Thr Lys Phe Leu Ser Tyr Lys Phe Ser
     75                  80                  85

AAC TCG GGG AGC AGA ATC ACC TGT GCA AAA CAG GAC TCC TGC AGA AGT    338
Asn Ser Gly Ser Arg Ile Thr Cys Ala Lys Gln Asp Ser Cys Arg Ser
 90              95                 100                     105

CAA CTG TGT GAG TGT GAT AAG GCT GCT GCC ACC TGT TTT GCT AGA AAC    386
Gln Leu Cys Glu Cys Asp Lys Ala Ala Ala Thr Cys Phe Ala Arg Asn
             110                 115                     120

AAG ACG ACC TAC AAT AAA AAG TAC CAG TAC TAC TCC AAT AAA CAC TGC    434
Lys Thr Thr Tyr Asn Lys Lys Tyr Gln Tyr Tyr Ser Asn Lys His Cys
             125                 130                     135

AGA GGG AGC ACC CCT CGT TGC TGAGTCCCCT CTTCCCTGGA AACC             479
Arg Gly Ser Thr Pro Arg Cys
             140
```

(2) INFORMATION FOR SEQ ID NO:10:

(i) SEQUENCE CHARACTERISTICS:
    (A) LENGTH: 144 amino acids
    (B) TYPE: amino acid
    (D) TOPOLOGY: linear (ii) MOLECULE TYPE: protein (xi) SEQUENCE DESCRIPTION: SEQ ID NO:10:

```
Met Lys Thr Leu Leu Leu Leu Ala Val Ile Met Ile Phe Gly Leu Leu
 1               5                  10                      15
```

| | | | | | | | | | | | | | | |
|---|---|---|---|---|---|---|---|---|---|---|---|---|---|---|
| Gln | Ala | His | Gly 20 | Asn | Leu | Val | Asn | Phe 25 | His | Arg | Met | Ile | Lys 30 | Leu | Thr |
| Thr | Gly | Lys 35 | Glu | Ala | Ala | Leu | Ser 40 | Tyr | Gly | Phe | Tyr | Gly 45 | Cys | His | Cys |
| Gly | Val 50 | Gly | Gly | Arg | Gly | Ser 55 | Pro | Lys | Asp | Ala | Thr 60 | Asp | Arg | Cys | Cys |
| Val 65 | Thr | His | Asp | Cys | Cys 70 | Tyr | Lys | Arg | Leu | Glu 75 | Lys | Arg | Gly | Cys | Gly 80 |
| Thr | Lys | Phe | Leu | Ser 85 | Tyr | Lys | Phe | Ser | Asn 90 | Ser | Gly | Ser | Arg | Ile 95 | Thr |
| Cys | Ala | Lys | Gln 100 | Asp | Ser | Cys | Arg | Ser 105 | Gln | Leu | Cys | Glu | Cys 110 | Asp | Lys |
| Ala | Ala | Ala 115 | Thr | Cys | Phe | Ala | Arg 120 | Asn | Lys | Thr | Thr | Tyr 125 | Asn | Lys | Lys |
| Tyr | Gln 130 | Tyr | Tyr | Ser | Asn | Lys 135 | His | Cys | Arg | Gly | Ser 140 | Thr | Pro | Arg | Cys |